US006589267B1

(12) United States Patent
Hui

(10) Patent No.: US 6,589,267 B1
(45) Date of Patent: Jul. 8, 2003

(54) HIGH EFFICIENCY EXTERNAL COUNTERPULSATION APPARATUS AND METHOD FOR CONTROLLING SAME

(75) Inventor: John C. K. Hui, East Setauket, NY (US)

(73) Assignee: Vasomedical, Inc., Westbury, NY (US)

( * ) Notice: Subject to any disclaimer, the term of this patent is extended or adjusted under 35 U.S.C. 154(b) by 127 days.

(21) Appl. No.: 09/710,692

(22) Filed: Nov. 10, 2000

(51) Int. Cl.[7] ................................ A61B 17/12
(52) U.S. Cl. ................................ 606/202; 601/152
(58) Field of Search ................................ 601/152, 151, 601/150, 148, 149; 606/201, 202, 203, 204

(56) References Cited

U.S. PATENT DOCUMENTS

| | | | |
|---|---|---|---|
| 2,230,068 | A | 1/1941 | Roensch |
| 2,249,579 | A | 7/1941 | Rea |
| 2,351,242 | A | 10/1944 | Rosett |
| 2,528,843 | A | 11/1950 | Poor |
| 2,533,504 | A | 12/1950 | Poor |
| 2,543,284 | A | 2/1951 | Gleason |
| 2,674,231 | A | 4/1954 | Erickson |
| 2,694,395 | A | 11/1954 | Brown |
| 2,747,570 | A | 5/1956 | Jobst |
| 3,063,444 | A | 11/1962 | Jobst |
| 3,094,116 | A | 6/1963 | Logan et al. |
| 3,179,106 | A | 4/1965 | Meredith |
| 3,303,841 | A | 2/1967 | Dennis et al. |
| 3,403,673 | A | 10/1968 | MacLeod et al. |
| 3,483,862 | A | 12/1969 | Takeuchi |
| 3,548,809 | A | 12/1970 | Conti et al. |
| 3,654,919 | A | 4/1972 | Birtwell et al. |
| 3,659,593 | A | 5/1972 | Vail |
| 3,712,290 | A | 1/1973 | Irnich et al. |
| 3,734,087 | A | 5/1973 | Sauer et al. |
| 3,783,859 | A | 1/1974 | Sauer et al. |
| 3,786,802 | A | 1/1974 | Hagopian et al. |
| 3,795,242 | A | 3/1974 | Lerch et al. |
| 3,835,845 | A | 9/1974 | Maher |
| 3,865,103 | A | 2/1975 | Folman |
| 3,866,604 | A | 2/1975 | Curless et al. |

(List continued on next page.)

FOREIGN PATENT DOCUMENTS

WO WO 99/08644 A2 2/1999

OTHER PUBLICATIONS

Vasomedical "EECP Therapy System Model TSJ", 2000.
American Society For Artificial Organs "Transactions", 1965.

*Primary Examiner*—Ismael Izaguirre
(74) *Attorney, Agent, or Firm*—Harness, Dickey & Pierce, P.L.C.

(57) ABSTRACT

The present invention provides a high efficiency external counterpulsation apparatus having accurate and reliable timing of inflation and deflation and reduced temperature of the pressurized gas, such that the gas flow temperature of the balloons is near to room temperature. The external counterpulsation apparatus also has a new gas distribution device and devices for monitoring the blood pressure and oxygen levels in the blood of a patient for improving safety. The present invention further provides a method for controlling the external counterpulsation apparatus.

23 Claims, 31 Drawing Sheets

U.S. PATENT DOCUMENTS

| | | | | |
|---|---|---|---|---|
| 3,878,839 | A | | 4/1975 | Norton et al. |
| 3,892,229 | A | | 7/1975 | Taylor et al. |
| 3,901,221 | A | | 8/1975 | Nicholson et al. |
| 3,942,518 | A | | 3/1976 | Tenteris et al. |
| 3,970,076 | A | | 7/1976 | Hepp et al. |
| 3,976,056 | A | | 8/1976 | Brawn |
| 4,013,069 | A | | 3/1977 | Hasty |
| 4,030,488 | A | | 6/1977 | Hasty |
| 4,080,958 | A | | 3/1978 | Bregman et al. |
| 4,091,804 | A | | 5/1978 | Hasty |
| 4,253,449 | A | | 3/1981 | Arkans et al. |
| 4,388,919 | A | | 6/1983 | Benjamin, Jr. et al. |
| 4,454,494 | A | | 6/1984 | Williams et al. |
| 4,753,226 | A | | 6/1988 | Zheng et al. |
| 5,245,990 | A | | 9/1993 | Bertinin |
| 5,429,584 | A | | 7/1995 | Chiu et al. |
| 5,443,440 | A | | 8/1995 | Tumey et al. |
| 5,487,722 | A | | 1/1996 | Weaver et al. |
| 5,554,103 | A | * | 9/1996 | Zheng et al. ............... 600/311 |
| 5,571,075 | A | | 11/1996 | Bullard et al. |
| 5,891,012 | A | | 4/1999 | Downey et al. |
| 5,997,540 | A | * | 12/1999 | Zheng et al. ............... 600/311 |
| 6,132,363 | A | | 10/2000 | Freed et al. |
| 6,144,880 | A | | 11/2000 | Ding et al. |

* cited by examiner

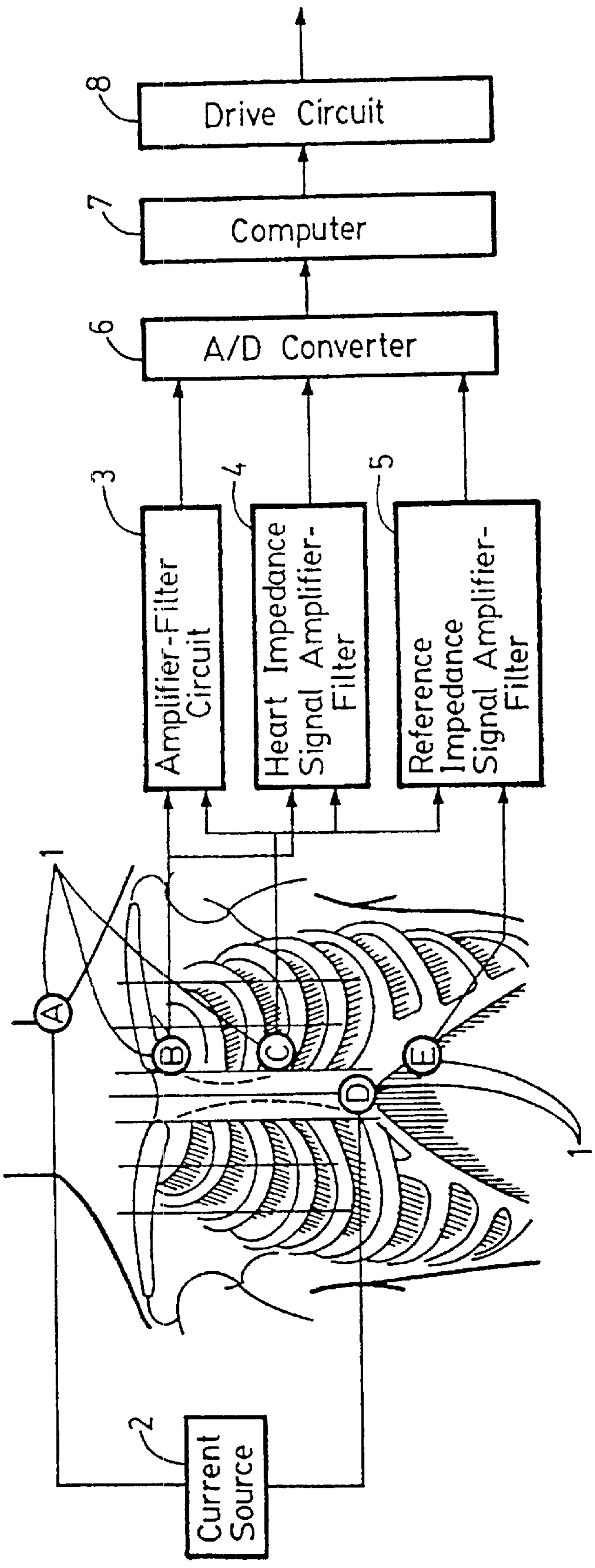
FIG.__4A.

Range for $T_1$ : 150ms ≤ $T_1$ ≤ ($T_x$ - 200ms)

Range for $T_2$ : ($T_1$ + 150ms) ≤ $T_2$ ≤ ($T_x$ - 30ms)

FIGURE 27
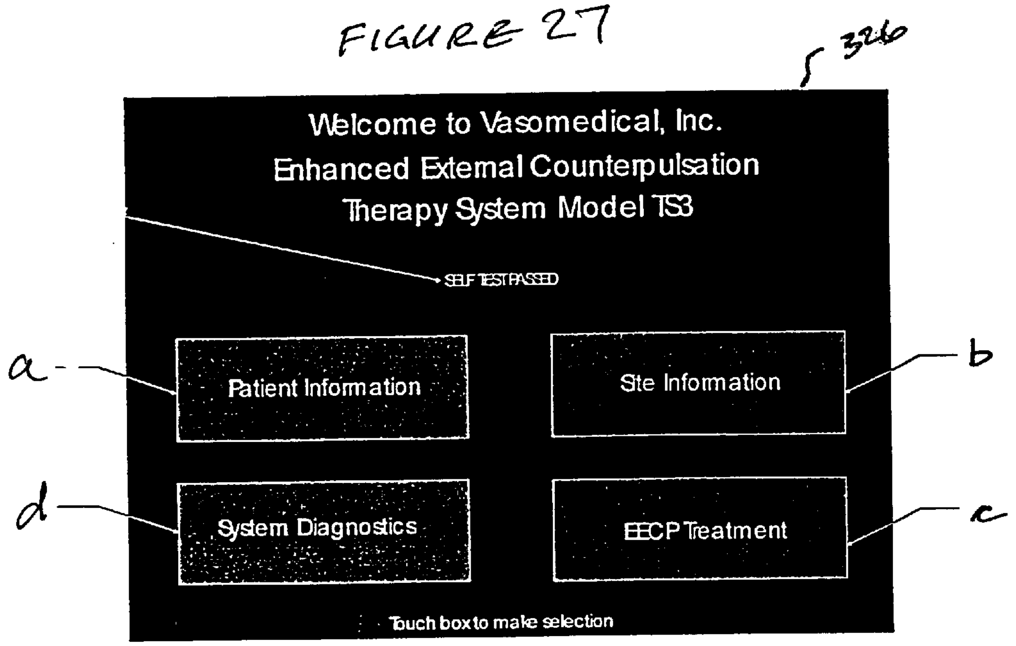
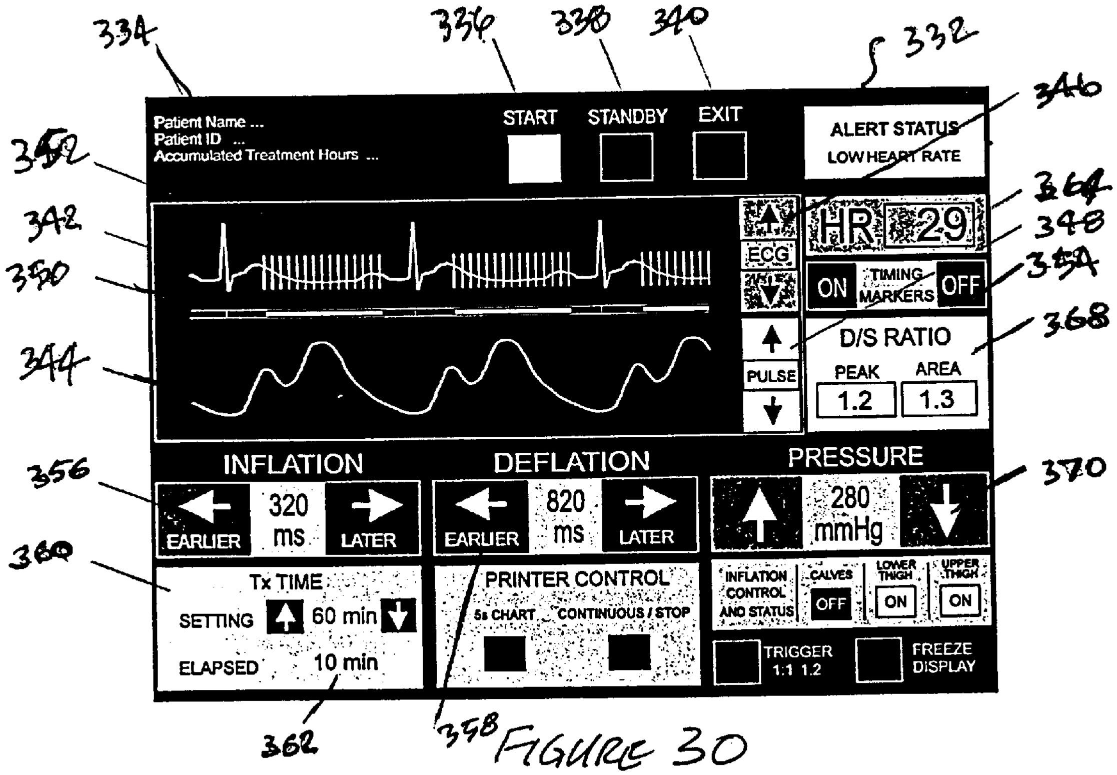
FIGURE 30

HIGH EFFICIENCY EXTERNAL COUNTERPULSATION APPARATUS AND METHOD FOR CONTROLLING SAME

BACKGROUND AND SUMMARY OF THE INVENTION

The present invention relates to an external counterpulsation apparatus and method for controlling the same, and more particularly, to such an external counterpulsation apparatus and method for controlling the same having improved efficiency and utility.

External counterpulsation provides tangible curative effect in the treatment of cardiovascular diseases, which have become more and more prevalent in recent years. In American Cardiovascular Journal (30(10)656–661, 1973) Dr. Cohen reported a device for external counterpulsation, being a four-limb sequential counterpulsation device. It consists of multiple balloons wrapped around the four limbs of the patient. Pressure is applied sequentially from the distal to the proximal portion of each limb. Using high pressure gas from a large compressor as its energy source (1000 to 1750 mm Hg) to control the opening time of a solenoid valve, the balloons receive pressurized air during inflation. The balloons are deflated by use of a vacuum pump. The device requires the use of a large air compressor, a large vacuum pump and the use of numerous pressure transducers to monitor the input pressure to insure that no excessive pressure is exerted in the balloons. However, this device is not only bulky and expensive, but it is also extremely noisy and complicated to operate. It is, therefore, unsuitable for everyday clinical use.

External cardiac assistance has been described in U.S. Pat. No. 3,866,604, which is an improvement on the above original external counterpulsation device. However, this device is extremely bulky noisy, and complicated to operate.

An external counterpulsation apparatus has also been described in Chinese patent CN85200905, which has also been granted as U.S. Pat. No. 4,753,226. This external counterpulsation apparatus is regarded as another improvement over previous art. In addition to balloons for the four limbs, it also comprises a pair of buttock balloons. The balloons are sequentially inflated with positive pressure and then, with appropriate delay, simultaneously deflated using a microcomputer to control the opening and closing of solenoid valves. The high pressure gas source and vacuum pump have been eliminated, so as to reduce the volume of the apparatus and make it more practical. However, the deflation of the balloons of this apparatus lacks the suction of negative pressure and depends on natural exhaustion into the atmosphere. Therefore the exhaustion of the balloons is incomplete and slow, and leaves behind residual gas in the balloon which hinders the ability of this device to reduce afterload (workload) of the heart.

A positive and negative enhanced type external counterpulsation apparatus has been described in Chinese patent CN88203328, wherein a negative pressure suction means for exhaustion of the balloons has been added. However, this apparatus is still ineffective in the exhaustion of all the pressurized gas in the balloons, and in addition, it is still too large, noisy and heavy for transport to be of practical application in the clinical setting.

A miniaturized external counterpulsation apparatus has been described in Chinese Patent CN1057189A, wherein the air compressor can be placed inside the main body of the device and does not require a separate embodiment. The box containing the solenoid valves and the balloon cuffs are suspended in a tube like apparatus and directly attached to the main body of the device. This device is practical for clinical use in that its size is very much reduced. However, this device does not have negative suction to increase the rate of deflation of the balloons, and it is still extremely noisy and not very efficient in producing desirable counterpulsation hemodynamic effects, namely, a high rate of inflation and effective deflation.

The foregoing external counterpulsation apparatuses have many advantages over the original one, but there are still many problems. For example, the high pressure air produced by the air compressor has a high temperature when it arrives at the balloons, which may cause discomfort feeling or even pain for the patient; the balloon cuff used by the prior art external counterpulsation apparatus is made of soft materials such as leatherette, canvas and the like, which may have a high elasticity and extensibility, requiring the use of a large volume of gas to achieve the required pressure and resulting in the inability to quickly inflate the balloons for optimal rate of inflation. Furthermore, dead space may be formed due to the misfit between the balloon cuff and the surrounded limb; the balloon cuff could slip downward during counterpulsing thereby being incapable of efficiently driving blood from peripheral regions to the root of the aorta, which directly affects the effectiveness of the counterpulsation treatment. All these factors reduce the efficiency of counterpulsation and require more pressurized gas to fillup dead space and more power from the compressor. At the same time a reduction in the rate of inflation of the balloon results which hinders the effective compression of the body mass as well as vasculature.

Historically, the earlobe pulse wave, finger pulse or temporal pulse wave is used as a timing signal to give the appropriate time for application of the external pressure so that the resulting pulse produced by external pressure in the artery can arrive at the root of the aorta just at the closure of the aortic valve. Thus, the arterial pulse wave is divided into a systolic period and a diastolic period. However, earlobe pulse wave, finger pulse wave or temporal pulse wave are signals derived from microcirculation and may or may not reflect the true pulse wave from the great arteries such as the aorta. Using the dicrotic notch as the true aortic valve closure is incorrect because the dicrotic notch is affected by many other factors such as the dampening effect of the vascular elasticity, reflective wave from tapering of the arteries and interference from previous pulse waves. Therefore it is most important in the art of external counterpulsation to find the true aortic valve closure time so the appropriate inflation time can be found for the externally applied pressure.

Theoretically, there are two factors that should be taken into account to determine the appropriate deflation time of all the balloons simultaneously. (1) release of all external pressure before the next systole to produce maximal systolic unloading, that is the maximum reduction of systolic pressure; (2) maintenance of the inflation as long as possible to fully utilize the whole period of diastole so as to produce the longest possible diastolic augmentation, that is the increase of diastolic pressure due to externally applied pressure. Therefore one measurement of effective counterpulsation is the ability to minimize systolic pressure, and at the same time maximize the ratio of the area under the diastolic wave form to that of the area under the systolic wave form. This consideration can be used to provide a guiding rule for determination of optimal deflation time.

Furthermore, the various existing external counterpulsation apparatuses only measure the electrocardiographic signals of the patient to guard against arrhythmia. Since counterpulsation applies pressure on the limbs during diastole, which increases the arterial pressure in diastole and makes it higher than the systoic pressure, the blood flow dynamics and physiological parameters of the human body may vary significantly. Some of these variations maybe advantageous, while some of them are potentially unsafe. For patients with arteriosclerosis and phlebosclerosis, there is the danger of blood vessels breaking due to the increase in their internal pressure. Furthermore, applying pressure to the limbs presses not only on the arteries but also the veins, and this may result in an increase in the amount of blood returning to the heart. This may cause cardiac lung or pulmonary edema because of the degration of the decrease in pumping capacity of the heart and incapability of the heart to pump out the increased amount of blood returning to the heart. This may, in turn, affect the oxygen saturation in the arteries of the body and cause an oxygen debt. It is therefore necessary to monitor the maximum value of the arterial pressure and oxygen saturation in the blood of a patient in addition to monitoring the electro-cardiogram, to ensure safety of the patient during the counterpulsation treatment.

Furthermore, the gas distribution device in the existing external counterpulsation apparatuses operate by controlling the opening and closing of the solenoid valves, which until now has the disadvantage of having voluminous and complex pipe connections. This is disadvantageous to miniaturizing the whole apparatus and improving its portability.

Accordingly, it is an object of the present invention to overcome the above disadvantages and provide an improved efficiency external counterpulsation apparatus having improved utility and accuracy.

It is another object of the present invention to provide an external counterpulsation apparatus having accurate and reliable timing of inflation gas flow temperature of the balloons is near to room temperature.

It is a further object of the present invention to provide a miniature external counterpulsation apparatus having a new gas distribution means and reduced pipe connections.

It is yet another object of the present invention to provide an external counterpulsation apparatus having devices for monitoring the blood pressure and oxygen saturation in the blood of a patient, and to monitor other complications arising from the treatment.

It is yet another object of the present invention in some embodiments, but not necessarily all embodiments, to provide a negative suction to the deflation of the balloons so as to effectively exhaust all pressurized gas rapidly, to lower the systolic pressure, and reduce the noise level of the solenoid valves.

It is yet another object of the present invention to provide a semi-rigid or rigid balloon cuff which can either be molded into the shape of the surrounded limb, or used in conjunction with inserts of suitable incompressible materials used to occupy the dead space between the balloon cuff and surrounded limb to effectively reduce the volume of compressed gas and power loss as well as the time required to raise the external pressure to the required level for compression of the underlying vasculature.

It is a further object of the present invention to provide a more efficient compressor for the use of external counterpulsation to produce the right volume of gas at the appropriate pressure, and which has reduced size, noise level and electrical power consumption.

To achieve some of the above objects of the invention, the present invention proposes an external counterpulsation apparatus, which comprises:

a first gas compressor;

a second gas compressor;

a control means;

a first positive pressure reservoir;

a second positive pressure reservoir;

a first negative pressure reservoir;

a second negative pressure reservoir;

a first solenoid valve;

a second solenoid valve;

a plurality of balloon devices, each of the balloon devices consisting of a balloon and a balloon cuff body which is made of a material of certain toughness and hardness, and fixing elements, wherein the shape of the balloon cuff body substantially matches the contour of the upper or lower limbs or the buttocks of the body;

a gas distribution means, comprising a cylinder and corresponding piston; a partition in the cylinder having a central hole therein which divides the cylinder into two portions, the piston also being divided into two portions, a first portion and a second portion, positioned one on each side of the partition, the two portions being connected by a rod passing through the central hole of the partition; a plurality of vents corresponding to said plurality of balloon devices which are symmetrically arranged on two sides of a first portion of the cylinder, each of the vents being connected to a corresponding one of the plurality of the balloon devices by pipes;

an outlet in this portion of the cylinder, which is connected to the first negative pressure reservoir by a pipe and to the second negative pressure reservoir via the second solenoid valve; the second portion of the piston is of an “I” shape and forms a cylindrical gas chamber within the cylinder, the axial length of the gas chamber being selected so that it communicates with each one of the symmetrically arranged vents as the piston moves towards the first portion of the cylinder; a first vent, a second vent in the second portion and a third vent in the first portion of the cylinder, wherein the first vent is connected to the first solenoid valve by a pipe, the piston being movable towards the first portion of the cylinder when gas is flowing from the first positive pressure reservoir into the cylinder via the first solenoid valve, the second vent being positioned between the first portion of the piston and the partition and also being connected to the first solenoid valve by a pipe so that gas may flow from the first positive pressure reservoir into the gas chamber and move the piston in the opposite direction towards the second portion of the cylinder; the position of the third vent is selected such that whatever position the piston is in, the vent will always communicate with the gas chamber formed by the second portion of the piston and the cylinder, the third vent is connected to the second positive pressure reservoir by a pipe; gas flow can sequentially inflate the plurality of balloons via the plurality of corresponding vents in the first portion of the cylinder as the piston moves across the plurality of vents; the outlet in the first portion of the cylinder being connected to the negative pressure reservoir by a pipe; when the balloons deflate the second solenoid is opened, and the gas in the balloons is discharged into the second negative pressure reservoir while discharging into the first negative pressure reservoir;

a control means, including a plurality of detector electrodes positioned at predetermined places on the body, a high frequency constant current source, filter means for electrocardiographic and impedance signals, and a computer system consisting of a micro-computer and A/D converters, the computer system operating to perform adaptive filtering of the impedance cardiograph, to obtain data for controlling the inflation and deflation time of the balloons, and to generate corresponding inflation and deflation signals; a drive circuit, responsive to said inflation and deflation signals, operating to automatically inflate and deflate the balloons, and to discharge the gas in the negative pressure reservoirs.

Preferably the counterpulsation apparatus of the present invention also comprises a blood pressure detector means, for monitoring the blood pressure of the patient during counterpulsation comprising; solenoid valves and throttle valve for inflating and deflating the cuffs, electromagnetic pressure transducers for sensing pressure inside the cuffs, electrophoto-transducers for measuring pulse wave and oxygen saturation of blood, and an amplifying and filtering processing circuit. The maximum pressure of the arterial pressure is monitored by a cuff occlusive indirect blood pressure measuring method. At the beginning of measurement, the inflating passage of the solenoid valve is opened, gas for pressurizing the lower limbs inflates the cuffs via pipes and solenoid valves. Pressure transducers monitor the pressure inside the cuffs. When the pressure rises to a certain value after occlusion of the arteries and the electrophoto-transducer can not detect the pulse wave, the solenoid valve opens the deflating passage and the gas in the cuffs slowly deflates via the solenoid valves and the throttle valves and the pressure inside the cuffs slowly drops. When the pressure inside the cuffs is equal to or slightly below the maximum pressure of the arteries (which is the systolic pressure before counterpulsation, and diastole counterpulsation pressure during counter pulsation) the occluded blood vessels are pushed open instantaneously and, at that time, a rapidly varying pulse wave can be detected by the electrophoto transducer, which indicates the arrival of the maximum pressure of the arteries. The pressure detected by the pressure transducer at that time is the maximum pressure. The apparatus preferably also includes a blood oxygen detector means, for monitoring the oxygen saturation in the blood during counterpulsation by the use of pulse blood oxygen measuring method. The transducer for pulse blood oxygen measurement cooperates with the electrophoto-transducer for detecting pulse waves in blood pressure measurement, and after amplifying and filtering, processing the saturation of blood oxygen is obtained by analyzing and calculating of the waveform by the micro-processor. When the blood pressure exceeds a predetermined value, or the blood oxygen saturation goes below a predetermined value, the computer issues a signal to stop the counterpulsation.

In addition, the present invention provides a method for controlling external counterpulsation apparatus, comprising the steps of:

(a) obtaining an impedance cardiograph during counterpulsation with stable waveform and the distinct characteristics such as the closure of the aortic valves using a plurality of electrodes and self-adaptive filtering technology;

(b) preforming self-adaptive filtering processing and detecting of the impedance cardiograph by the use of a micro-computer to obtain the closing point of the aortic valves and the starting point of the counterpulsation wave. The proper inflation time of the balloon cuffs can then be accurately determined by moving the starting point of the counterpulsation wave to coincide with the aortic valves closing time. In case there is too much noise in the impedance cardiograph such that determination of the aortic valves closure is impossible, then the inflation will be set at the end of the T wave of the electrocardiogram or using the method described in U.S. Pat. No. 4,753,226.

(c) using impedance cardiograph to detect the peak amplitude and duration of the systemic systolic blood pressure and the amplitude and duration of the pulse wave created by counterpulsation to calculate objective index such as the ratio of peak diastolic to peak systolic blood pressure as well as the ratio of the area under the systolic and diastolic pulse wave as indications of the hemodynamic effectiveness of counterpulsation; and (d) the ability to determine the ratio of the areas under the diastolic and systolic pulse waves provides means to adjust the deflation time in such a way as to maximize this ratio. However the adjustment of the deflation time in maximizing the reduction of the systolic blood pressure is more important than maximization of the ratio under the diastolic and systolic pulse wave; and (e) controlling the inflation and deflation times of the external counterpulsation apparatus with a computer Preferably, the method may also comprise the steps of:

(f) detecting the blood pressure state of the patient with a blood pressure detector means during counterpulsation to improve safety, and stopping counterpulsation when the blood pressure exceeds a predetermined value.

(g) detecting the blood oxygen saturation of the patient with a blood oxygen detector means during counterpulsation to improve safety, and stopping counterpulsation when the oxygen saturation goes below a predetermined level.

The advantages of the present invention lie in reduced gas consumption and effective counterpulsation, thereby reducing the burden on the gas compressor. In addition, discomfort or pain to the patient is reduced, and the burden on other environmental conditions is reduced as well, while the portability of the counterpulsation apparatus can be increased. Another significant advantage of the present invention lies in the non-invasive detection of the maximum arterial pressure and oxygen saturation of the blood of the patient, thereby guaranteeing the safety of the patient during counterpulsation treatment. And, more importantly, new control means and methods are adopted by the present invention, which make the inflation and deflation times of the counterpulsation apparatus more accurate and reliable, and improve the safety levels of counterpulsation treatment.

Still further objectives of the present invention are to provide enhanced ease of use and accuracy for the operator, patient data and other external interfaces in order to improve and enhance patient data updates and operator training and assistance, to provide for faster and more responsive inflation and deflation of the balloon inflatable devices, to provide normally-open deflation/exhaust ports on the inflation/deflation valves so that the pressure in the balloon inflation/deflation devices defaults to exhaust, especially in the event of a power failure, to provide an improved and more balance flow rate during deflation or exhaust as compared to inflation, to provide for greater ease of obtaining patient comfort and enhanced equipment mobility, as well as smoother operation and more optimized power usage, especially during system startup.

The above and other objects, advantages and features of the present invention will be better appreciated with reference to the following discussion, the accompanying drawings and the claims.

BRIEF DESCRIPTION OF THE DRAWINGS

FIGS. 4A and 4B are detailed block diagrams of the control means in the external counterpulsation apparatus according to the present invention.

FIG. 27 illustrates an exemplary main menu control screen for the enhanced computer system of the present invention.

FIG. 30 illustrates an exemplary treatment control screen for the enhanced computer system of the present invention.

DETAILED DESCRIPTION OF THE PREFERRED EMBODIMENTS

A detailed description of varied and merely exemplary embodiments of the present invention follows with reference to the accompanying drawings. One skilled in the art will readily recognize that the principles of the invention are equally applicable to other embodiments and applications.

Figure 1:
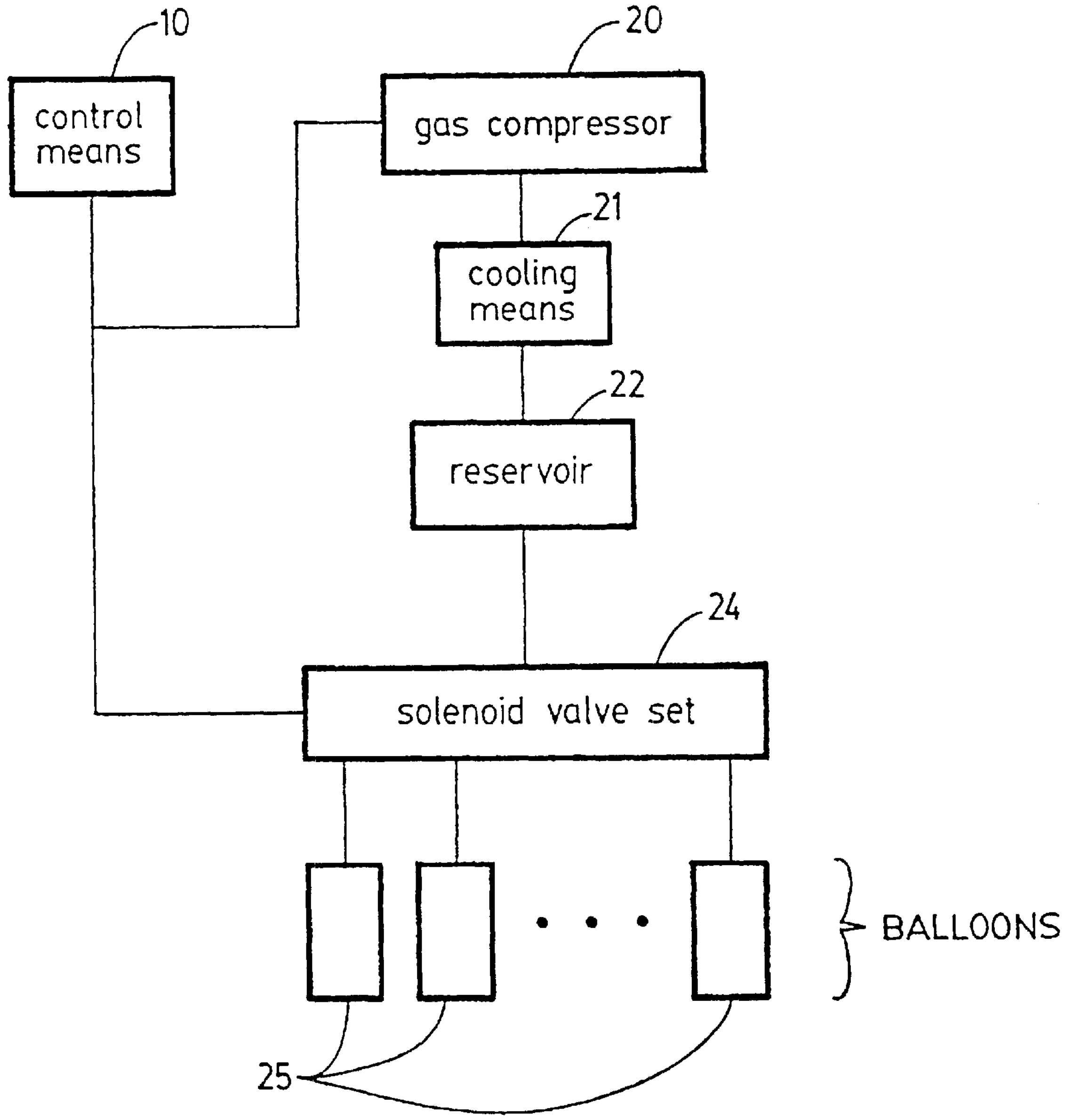
FIG. 1 is a block diagram of a first embodiment of the external counterpulsation apparatus according to the present invention.

FIG. 1 is a block diagram of a first exemplary embodiment of an external counterpulsation apparatus according to the present invention, wherein a control means 10 controls the gas compressor 20 and set of solenoid valves 24. The compressor can be of rotary vane type, piston type, diaphragm or blower type. However, one preferred embodiment is a scroll type compressor as described in the Chinese Patent CN1030814A which essentially consists of two scroll basin with very narrow gaps between them; with one scroll basin adapted to rotate at very high speed (3,000 rpm) while the other scroll basin remains stationary. The clenching of the scroll basins compresses the air radially inwardly toward the center and the compressed air comes out of the center shaft. The scroll type of compressor is more efficient in operation, more quiet and smaller in size than other types of compressors and therefore suitable for external counterpulsation apparatus described hereof. During operation, the compressor 20 operates to produce pressurized gas, preferably pressurized air, which is sent into the positive pressure reservoir 22 via the cooling means 21. A pressure limiting valve 23 is provided on the reservoir 22, which keeps the internal pressure of the reservoir 22 constant. The opening and closing of the set of solenoid valves 24 is controlled by the inflation and deflation driving signals generated by the control means in accordance with the heart impedance blood flow graph of the human body. The set of solenoid valves 24 include a number of two-position-three-way solenoid valves corresponding to the number of balloons 25. When a valve is in the first of the two positions, it inflates its balloon, when it is in the second of the two positions, it deflates its balloon, under control of the control system.

Figure 2:
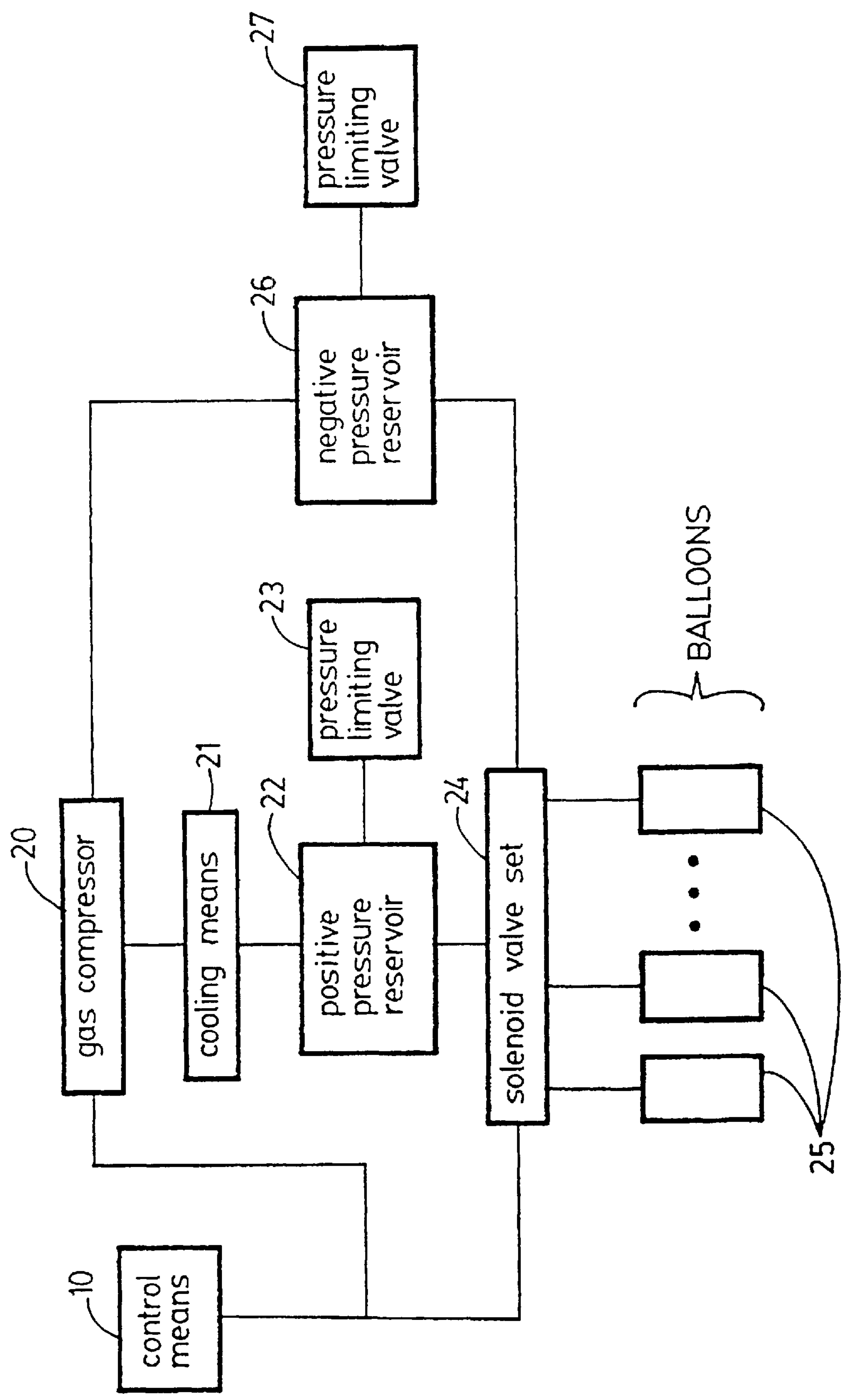
FIG. 2 is a block diagram of a second embodiment of the external counterpulsation apparatus according to the present invention.

FIG. 2 illustrates a second exemplary embodiment of an external counterpulsation apparatus according to the present invention. In this embodiment, a control signal is first generated by the control means 10, then the compressor 20 operates to compress gas into the positive pressure reservoir 22 after being cooled by the cooling means 21. A pressure limiting valve 23 is provided on the positive pressure reservoir to keep its internal pressure constant. A negative pressure reservoir 26 connected to the inlet of the compressor 20 produces negative pressure. The control system 10 controls the opening and closing of the set of solenoid valves 24 by issuing inflating and deflating driving signals in accordance with the results of detection. Again, when the set of solenoid valves 24 are in the first position, they inflate the balloons 25, when they are in the second position, they deflate the balloons 25. The gas discharged from the balloons is discharged into the negative pressure reservoir 26 via the set of solenoid valves 24, and then returns to the compressor 20. As there may be leakage during the circulation of gas, which may affect the amount of gas output from the compressor, a pressure limiting valve 27 is provided to adjust the negative pressure in the negative pressure reservoir. When the negative pressure exceeds a certain value, the pressure limiting valve 27 is opened to inject a certain amount of gas into the reservoir 26.

Figure 3:
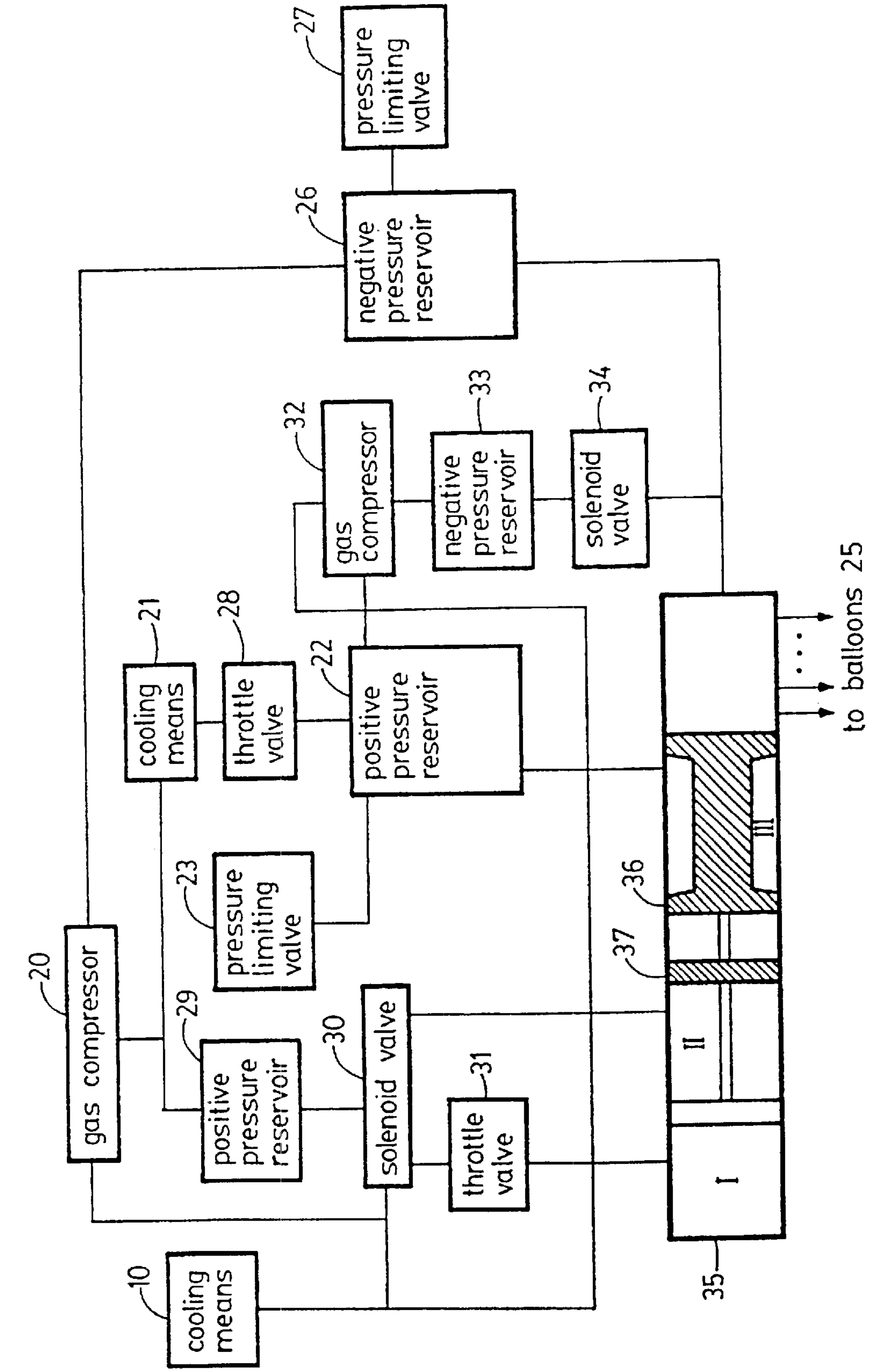
FIG. 3 is a block diagram of a third embodiment of the external counterpulsation apparatus according to the present invention.

FIG. 3 illustrates a third exemplary embodiment of an external counterpulsation apparatus according to the present invention; wherein the control system 10 generates control signals and the compressor 20 operates to produce two portions of pressurized gas, one portion of pressurized gas is sent to the positive pressure reservoir 29, while another is sent into the positive pressure reservoir 22 via the cooling means 21 and the throttle valve 28. The pressure limiting valve 23 is operative to adjust the pressure inside the reservoir 22. The reference numeral 30 indicates a two-position-five-way solenoid valve or two two-position-three-way solenoid valves, 31 indicates a mono-directional throttle valve, 35 indicates a cylindrical gas distribution means or cylinder, 37 is a partition and 36 indicates a piston. When an inflation driving signal is issued by the control means, the solenoid valve 30 opens to the first of the two positions, and the gas flow is introduced into the portion I of the cylinder from the reservoir 29 via the solenoid valve 30 and the throttle governor 31 to push the piston from a first towards a second end of the cylinder. A space portion III is formed by the piston and the cylinder and is always in communication with the reservoir 22, and vents for the balloons 25 are situated in sequence in the cylinder, the balloons being sequentially inflated as the piston moves towards the second end of the cylinder. When a deflation signal issued by the control means, the solenoid valve 30 is moved to its second position, and the gas in the reservoir 29 enters the portion II of the cylinder via the solenoid valve 30 to push the piston back to the first end of the cylinder. At that time, the gas in portion I is discharged via the solenoid valve 30, and the gas in the balloons is discharged to the negative pressure reservoir 26. In order to speed of deflation, a solenoid valve 34 is also opened at the same time and the gas discharged from the balloons is discharged to both negative pressure reservoirs 26 and 33. Negative pressure reservoir 33 is kept at a negative pressure by the input portion of compressor 32. Discharged gas is also sent to the reservoir 22 by the output portion of compressor 32.

During the deflation phase, in such an embodiment, if the pressurized balloon is simply exhausted into the atmosphere, exhaustion of the balloon may not be completed, with the residual gas pressing on the tissue mass surrounded by the balloon cuffs, reducing the much needed vascular space in the body to receive the volume of blood ejected by the heart. This might reduce the ability of counterpulsation to unload systolic blood pressure and reduce cardiac workload. The addition of negative pressure reservoirs 26, 33 serves to effectively and rapidly evacuate the pressurized gas in the balloons at the onset of systole, thereby ensuring complete absence of pressure on the lower extremities, enabling the vasculature which has been previously compressed and emptied during the diastolic period to act as suction to help the heart to eject blood out and unload the systolic blood pressure. In addition, and equally important, the addition of the negative pressure reservoirs 26, 33 ensures the smooth operation of the solenoid valves and prevents the leakage of large volumes of pressurized gas exhausting into the atmosphere. This closed gas system reduces the escape of noises generated by the opening and closing of solenoid valves and movement of air. It should be noted, however, that a negative pressure reservoir might not necessarily be required in other embodiments or applications of the principles of the present invention.

Furthermore, during normal operation of external counterpulsation, there is always some leakage of compressed air from the balloon during the inflation period. In order to compensate for the leakage of air to ensure there is adequate air for the intake of the compressor 20 to produce air pressure in the range of 5 to 15 psi, a leakage compensation means such as the use of a vacuum limiting valve, a vacuum pump or compressor or some combination thereof is provided. An example of the compensation means is a vacuum limiting valve 27 connected to the negative pressure reservoir 26, set at approximately negative 100 mm Hg. When the negative pressure reservoir is less than 100 mm Hg, the vacuum limiting valve is open and air is sucked into the reservoir to provide more air for the in take of the compressor 20.

Prior art in external counterpulsation often makes use of bulky, noisy and power consuming solenoid valves are normally closed to reduce the generation of heat in keeping them open. However, this situation would induce danger to the patient in case of power failure if compressed gas is trapped in the balloons.

Some embodiments of the present invention provide a gas cylindrical distribution system 35 as shown in FIG. 3, using a syringe system in pushing a piston in one direction to provide sequential inflation of the balloons, with the balloons 25 (not shown) furthest from the heart being inflated first. The balloons openings are placed on both sides of the cylinder, connecting to the left and right limbs as well as buttock. The number of balloons can be 2 to 8 or more on each side. This is achieved by connecting the balloons furthest from the heart to the portion of the cylinder closest to the piston, as the piston 36 moves from left to right as shown in FIG. 3. This gas distribution system uses compressed air to move a piston back and forth along a cylindrical means, producing a quiet operation without the need of too much power as compared to the use of bulky, noisy and power consuming solenoid inflation and deflation valves, thereby eliminating one of the most noisy parts of the prior art external counterpulsation apparatus, and reducing substantially the consumption of electric power. More importantly, the solenoid valve 30 is a normally open valve to portion II of the cylinder 35, thereby connecting portion II to the positive pressure reservoir 29 in case of power failure, moving the piston to the left of FIG. 3, exposing all the balloons to the negative pressure reservoir, thereby deflating all balloons and reduces the possibility of inducing trauma to the patient.

Figure 4B:
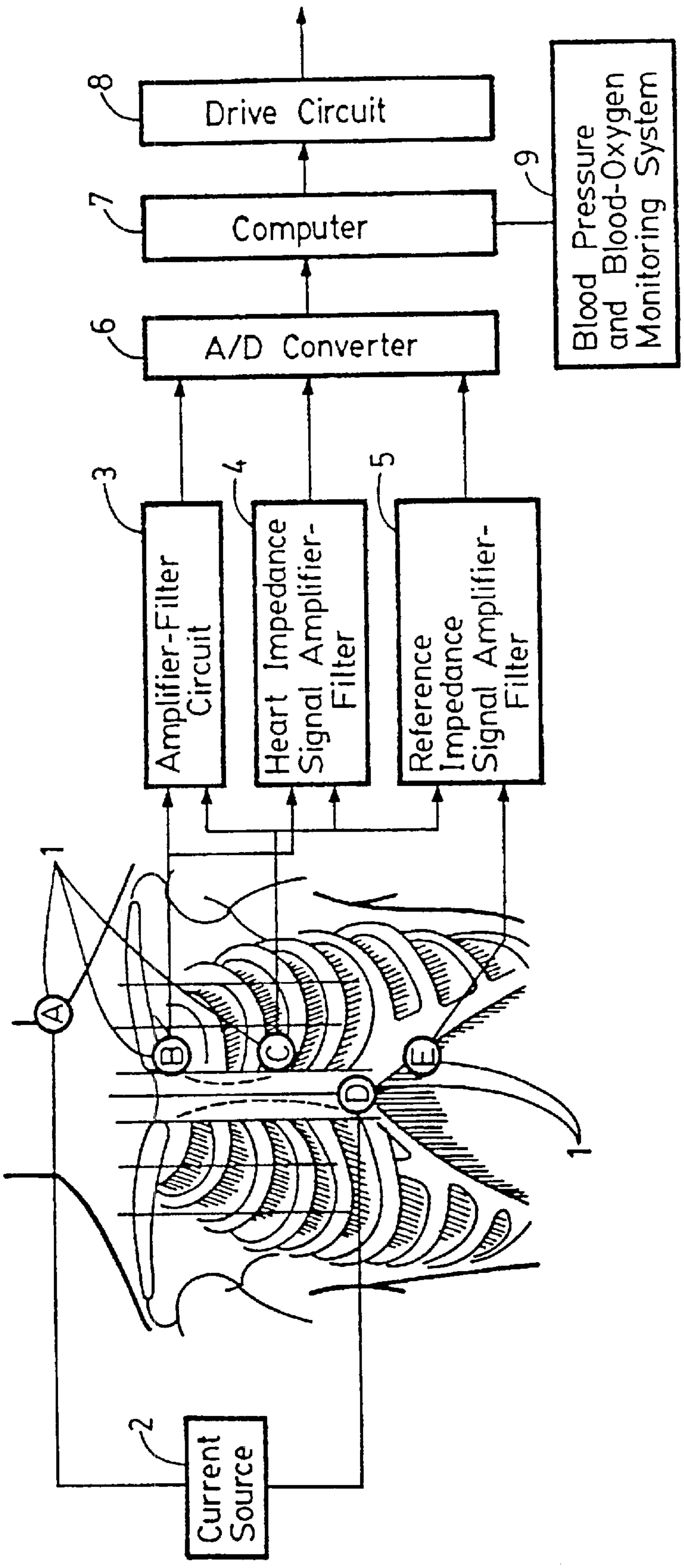

FIGS. 4A and 4B are detailed block diagrams of one exemplary control system in the external counterpulsation apparatus according to the present invention. Using impedance cardiography as the control means in detecting blood flow in the great arteries, the precise closure of the aortic valves and the pulse wave generated by external counterpulsation pressure in the external counterpulsation apparatus according to the present invention, wherein the reference numeral 1 indicates electrodes. The locations and types of electrodes used are for illustrative purposes and should not be considered as constraint to such design and configuration.

In these embodiments, the detecting electrode 1 consists of five point electrodes placed in positions shown in FIG. 4A, that is: electrode A positioned at the root of the left ear or mastoid, electrode D positioned at the xiphoid process, electrode B positioned at the lift edge of the left sternum below the clavicle and electrode C positioned at the lift edge of the left sternum between the fourth and fifth rib. Electrodes A and D are both impedance current electrodes, high frequency constant current being applied to the body from these two electrodes. Electrates B and C are both detector electrodes for measurement of the blood flow impedance signals which may be derived from blood flow in the great arteries in the thoracic space A reference electrode E is positioned in the left anterior of the 10th rib, signal obtained between electrodes C and E will be used as reference signal for measuring movement of the body, especially motion artifact produced during the application of external counterpulsation pressure. The location of the reference electrode E is not important but should be further away from the thoracic space.

Before the start of external counterpulsation treatment, high frequency constant current is applied to electrodes A and D, and blood flow impedance signals related to the blood flow in the great arteries in the thoracic space will be picked up by detector electrodes B and C; these blood flow impedance signals also contain a dip in the wave form indicating the closure of the aortic valves.

Because of the location of the reference electrodes pair C and E, the blood flow impedance signals detected between these electrodes will be much weaker than the signals detected by electrodes B and C. Upon initiation of external counterpulsation, there will be two additional signals detected by both pairs of detecting electrodes B, C and reference electrodes C and E, they are the retrograde blood flow impedance signals produced by the counterpulsation pressure, and the motion artifact produced by the same. The signals from motion artifact will present themselves to both pairs of electrodes in approximately equal amplitudes, while the signals from counterpulsation will be larger in the reference electrodes than in the detector electrodes because of the location of the reference electrodes in closer proximity to the counterpulsation hemodynamic effects. Consequently, subtraction of reference impedance signals from the detector impedance signals will provide a fairly clean blood flow impedance signals containing the time of aortic valves closure as well as the retrograde flow from counterpulsation. This kind of signal processing is known as self-adaptive filtering processing. By adjusting the onset of the inflation of the balloons, the retrograde blood flow signals can be advanced or retreated to coincide with the aortic valve closure thereby providing optimal counterpulsation timing. In addition, the adjustment of the optimal timing can also be performed by computer.

A high frequency constant current source 2 consists of: a transistor oscillator, amplitude limiting amplifier, band-pass filter and voltage-current converter to obtain a stable high frequency and stable amplitude current which is applied to the body by electrode A to measure the impedance.

An amplifier-filter circuit 3 for the electro-cardiographic signal consists of: a low-pass differential amplifier and band-pass filter-amplifier, which amplifies and filters the electrocardiographic signals of the body obtained from electrodes B and C.

A heart impedance signal amplifier-filter circuit 4 and a reference impedance signal amplifier-filter circuit 5 for adaptive processing consist of a band-pass filter-amplifier, a detector, a low-pass filter, and a differential circuit, signal amplifier-filter circuits amplify and filter the heart impedance blood flow signals obtained from the electrodes B and C, and the adaptive processed impedance reference signals obtained from the electrodes C and E.

A computer system can include a personal microcomputer 7 and an A/D converter 6. The A/D converter converts the electrocardiographic signals, heart impedance blood flow signals, and impedance reference signals into digital signals and inputs them into the computer. The computer displays the waveform, detects the QRS wave of the electrocardiogram indicates the upper and lower limits of the pulse rate, performs adaptive processing of the impedance blood flow signals and the impedance reference signals, measures the waveform's characteristic points such as the aortic valves closure and end diastolic and systolic amplitudes, and controls the inflation and deflation time of the external connterpulsation apparatus through a drive circuit 8.

FIG. 4B is also a detailed block diagram of an exemplary control system in the external counterpulsation apparatus according to the present invention, wherein a blood-pressure and blood oxygen monitoring means 9 are further added to the basic system shown in FIG. 4A.

Figure 4C:
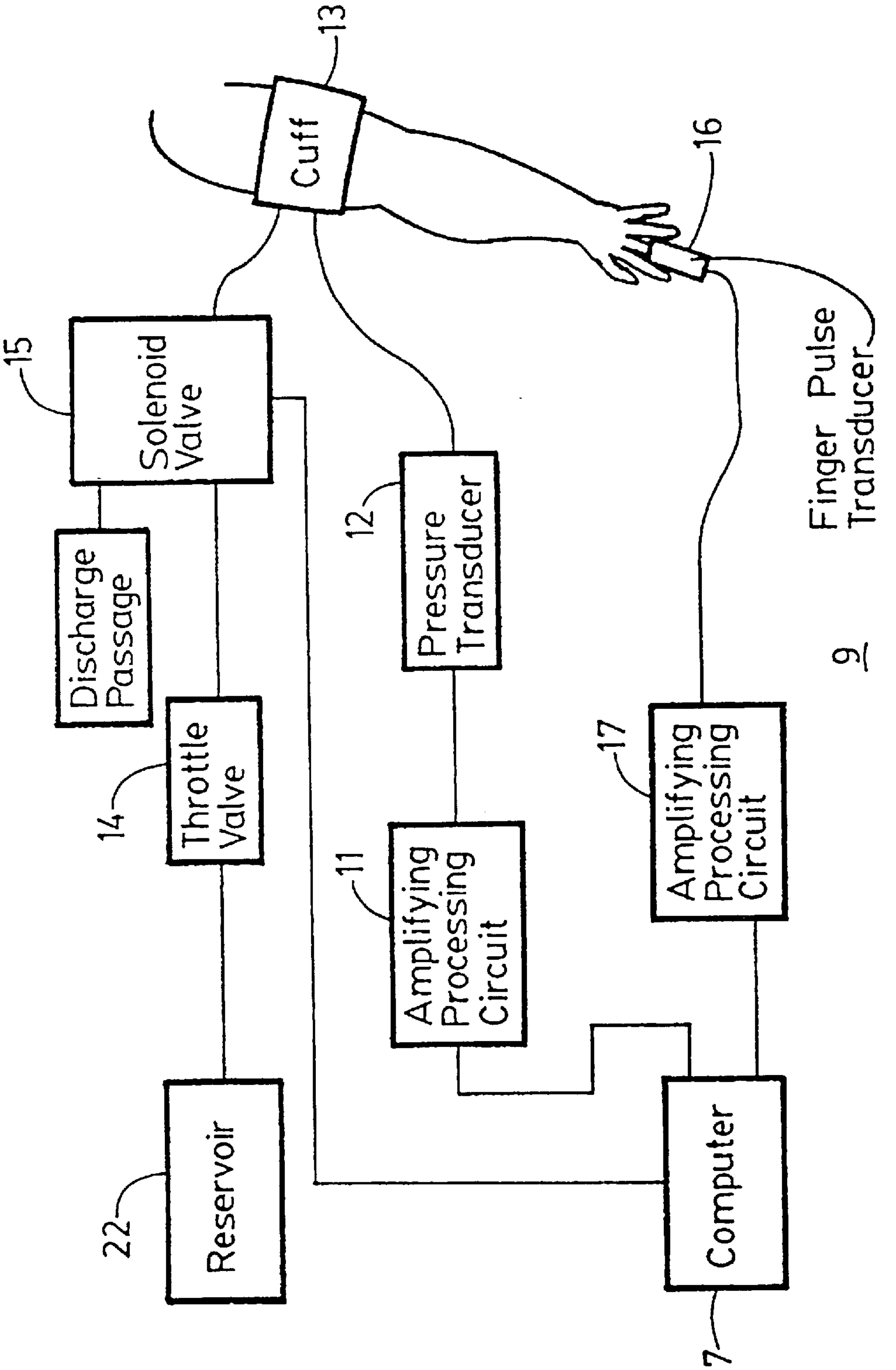
FIG. 4C is a detailed block diagram of the blood pressure and blood oxygen monitoring means illustrated in FIG. 4B.

FIG. 4C is a schematic block diagram of the blood-pressure and blood oxygen monitoring means 9 indicated in FIG. 4B.

Figure 4D:
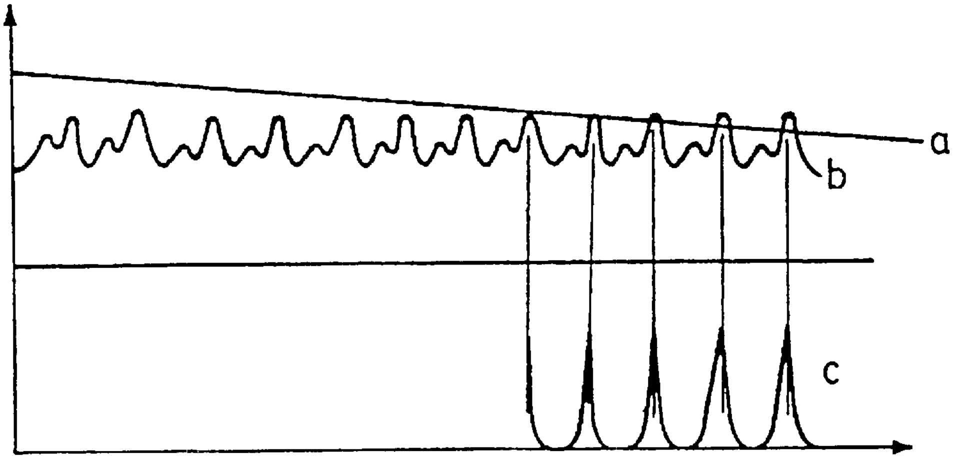
FIG. 4D is a schematic diagram showing the relationships between the variation of cuff pressure, finger pulse wave, and opening and closing of the aortic valves.

FIG. 4D is a schematic diagram showing the relationships between the pressure variation of the cuff, finger pulse wave, and the opening and closing of the aortic valve.

Figure 11:
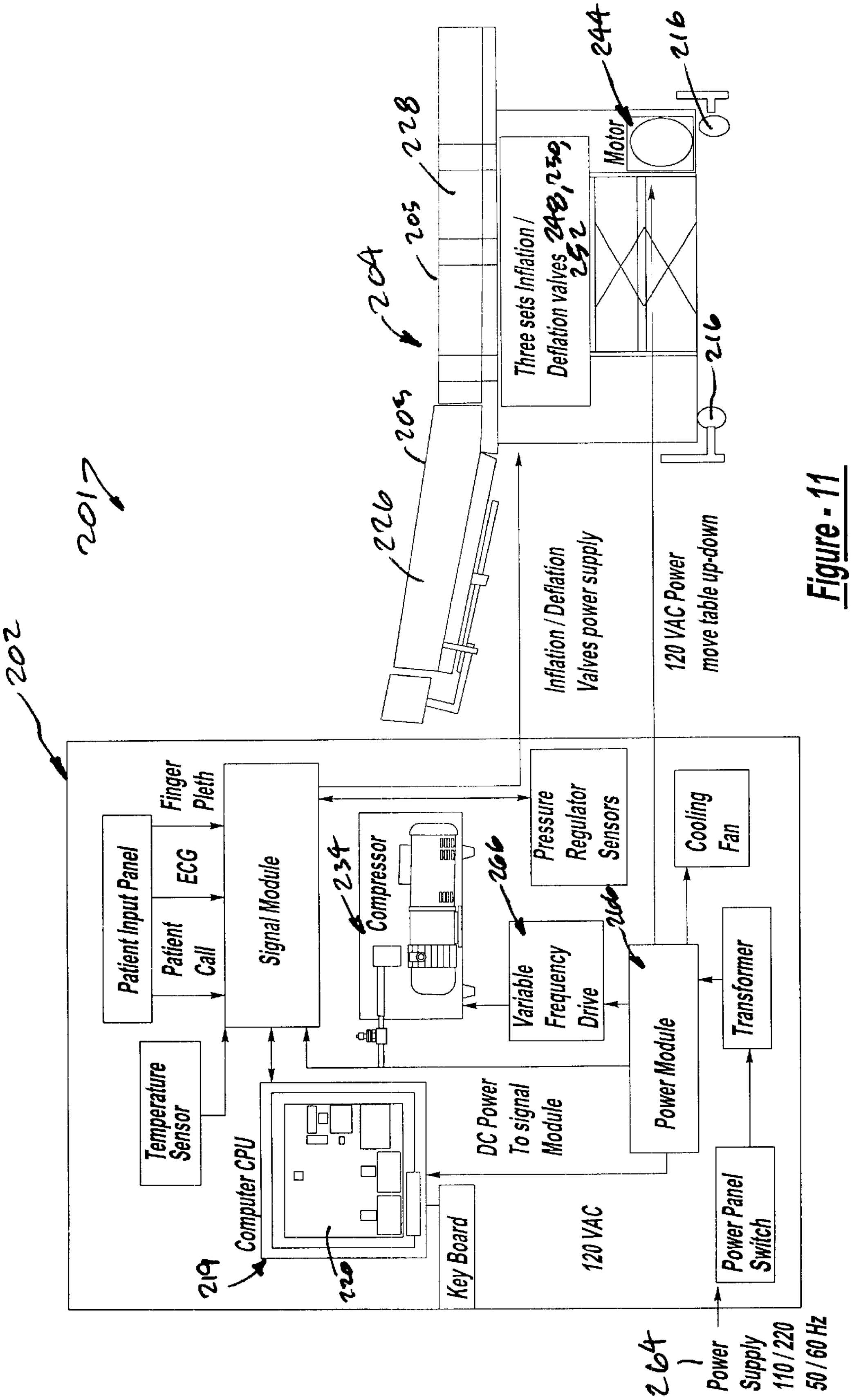
FIG. 11 is a control diagram for the external counterpulsation apparatus of FIGS. 8 through 10.
Figure 22:
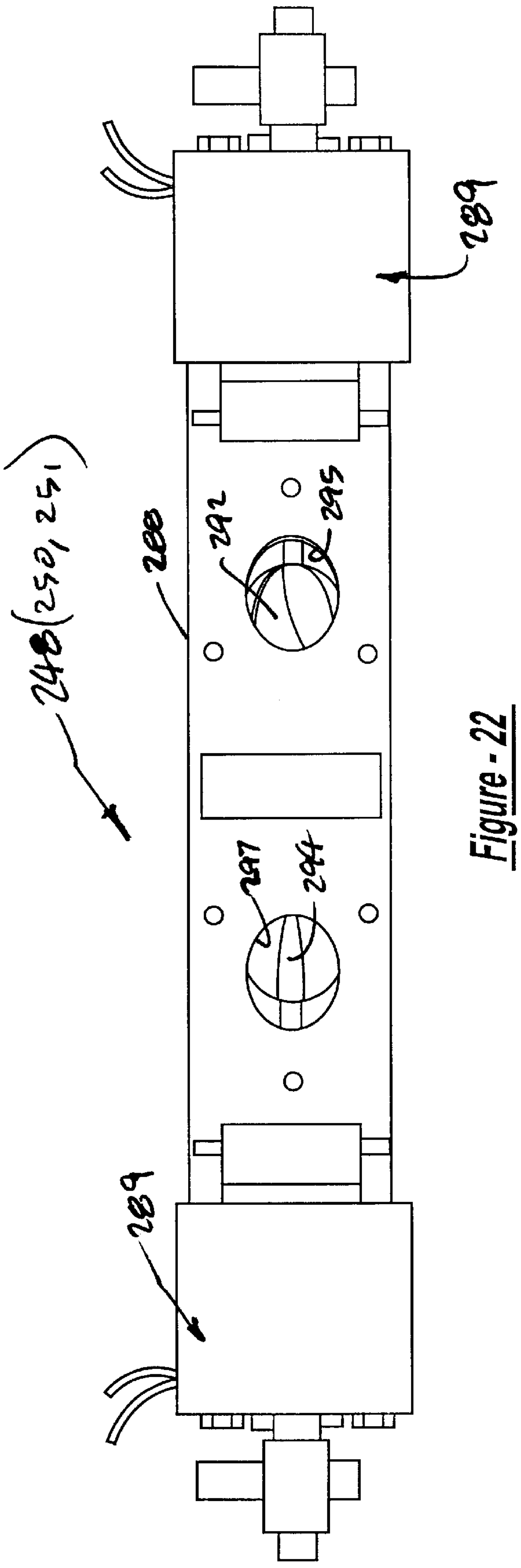

Referring to FIG. 4C, 22 indicates the reservoir of the counterpulsation apparatus, which inflates a cuff 13 via a pipe, throttle valve 14, and a passage in a solenoid valve 15. The solenoid valve is a two-position three-way valve controlled by the computer 7. The other passage of the solenoid valve is a discharging passage for the cuff, the discharge speed being controlled by the throttle valve 14. At the beginning of blood pressure measurement, the inflation passage of the solenoid valve 15 is opened, the pressurized gas in the reservoir 22 inflates the cuff 13 via the throttle valve 14 to a predetermined pressure value at which the arteriae are blocked. When they are blocked, a finger pulse transducer 16 is unable to detect a pulse wave. The inflating passage of the solenoid valve 15 is closed and the deflating passage is opened, the gas in the cuff discharges slowly via the solenoid valve 15 and the throttle valve 14 and the pressure inside the cuff drops slowly as shown by curve "a" in FIG. 4D. When the pressure in the cuff is equal to or slightly lower than the maximum arterial pressure, as shown by curve "b" in FIG. 4D, (systolic pressure before counterpulsation, and diastolic counterpulsation pressure during counterpulsation), the blocked blood vessels are pushed open instantaneously. At that time, the finger pulse transducer 16 will detect a rapidly varying pulse wave as shown by curve "c" in FIG. 4D. This indicates the arrival of the maximum pressure of the artery. The pressure detected by a pressure transducer 12 at that time is the maximum arterial pressure. Referring to FIG. 4C, 11 indicates an amplifying processing circuit for the pressure signal, and 17 indicates an amplifying processing circuit for the pulse signal. The amplified pressure and pulse signals are collected and processed by the computer 7 for performing corresponding counterpulsation control and calculation of oxygen saturation of blood.

It is a physical law that when air is compressed, heat will be generated. In external counterpulsation, approximately 25 cu. ft. of air is compressed to 5 to 15 psi pressure, generating a gas with temperature reaching as high as 90 to 100 degrees C., depending on the environment and efficiency of the compression means. When compressed gas with such high temperature is sent to the balloons which are in close contact with the patient's skin, it will produce abrasion or burn to the skin, or at the least, uncomfortable feeling to the patient. Therefore it may be necessary in some embodiments of this invention to provide means to cool the compressed air. In general, any means of cooling can be utilized in this invention, including exposure to the atmosphere of a long piece or coil of metal pipe connecting the compression means to the positive pressure reservoir, use of a fan to force air to blow through a coil of metal pipe carrying the heated gas, water cooling such as that used in the radiator of automobile, running water cooling, air conditioner.

Figure 5A:
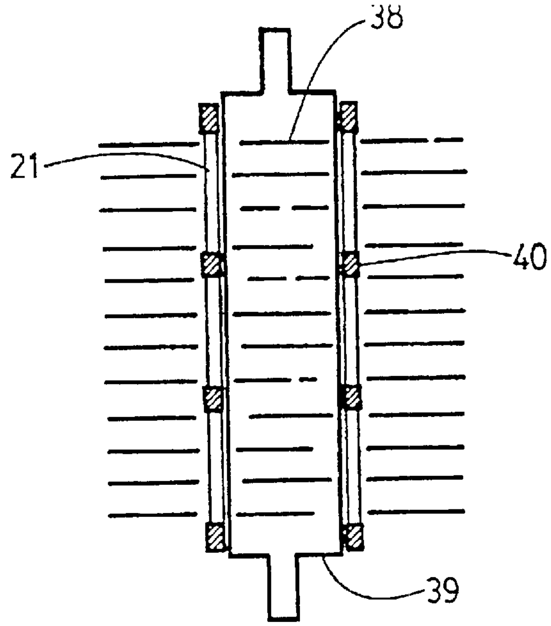
FIGS. 5A and 5B are partial schematic diagrams of the gas source portion in the external counterpulsation apparatus according to the present invention, illustrating gas pipes connected to a semiconductor cooling device and air-conditioner cooling evaporator, respectively.
Figure 5B:
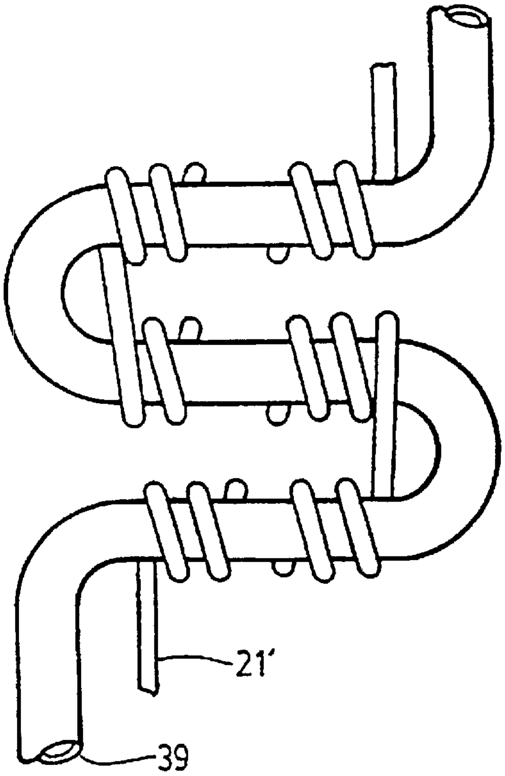

FIGS. 5A and 5B are partial schematic diagrams of the gas or compressed air source portion of the external counterpulsation apparatus according to the present invention, illustrating the gas pipes connected to a semiconductor cooling device and an air conditioner cooling evaporator, respectively, 21 and 21 indicate a semiconductor cooling device and an air conditioner cooling evaporator, respectively, 39 indicates a transmitting pipe, 38 indicates fins and 40 indicates heat isolation materials.

Prior art external counterpulsation apparatus often utilized materials such as vinyl, leather, cloth or canvas to make the balloon cuffs. These cuffs are wrapped tightly around the lower limbs with balloons put in between the cuffs and the body. When compressed gas is inflated into the balloons, the cuff will also expand and extend outward due to the elasticity and extensibility of its material, causing significant energy loss since a large portion of the compressed air serves to deform the cuff. More importantly, when compressed air is used to expand and extend the cuffs outwardly the pressure inside the balloons will not be built up quickly, reducing the rate of compression of the tissue mass and the underlying vasculature, causing a slower external counterpulsation pulse wave moving up the aorta. This reduces the effectiveness of counterpulsation in increasing the perfusion pressure to the coronary arteries and, therefore, the development of collateral circulations (i.e. a set of new vessels formed in the myocardium (heart) bypassing the blockages in the coronary arteries). Therefore, the present invention can provide for the use of rigid or semi-rigid materials with little or no extensibility and elasticity so that the introduction of compressed air into the balloons will not cause the deformation or expansion of the cuffs, thereby requiring less pressurized air and reducing energy loss. Furthermore, the use of rigid or semi-rigid materials in making the cuffs will result in rapid filling of the balloons, quicker compression of the surrounded tissue mass and therefore a steeper external counterpulsation leading pulse wave travelling retrogradedly up the aorta to the heart.

Figure 6:
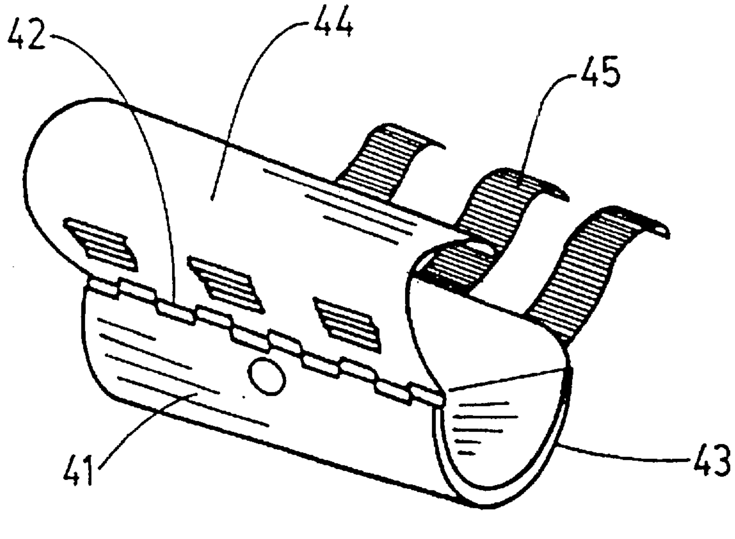
FIG. 6 is a schematic diagram of the balloon device used in the external counterpulsation apparatus according to the present invention, illustrating an improved structure of the balloon cuff body.

FIG. 6 is a schematic diagram of the balloon device 41 in the external counterpulsation apparatus according to the present invention. A balloon cuff body 44 surrounding the balloon 25 (not shown) is made of materials of certain toughness and hardness such as plastic (e. g. polyacrylate), aluminum, or other metallic plates, rather than of leather cloth and canvas, thereby reducing the inflatability and extendibility of the balloon cuff body can be reduced substantially. Tubular balloon cuff bodies can be fabricated to fit the upper limbs, lower limbs and other balloon cuff bodies can be fabricated to fit the buttocks, such that the balloon cuff body tightly surrounds the body without gaps, and is prevented from slipping. Different sizes of balloon cuffs body should be provided to meet the requirements of different body shapes. The balloon cuff body 44 can be pre-fabricated or preformed or formed out of thermally changeable materials in whatever form is necessary. There are materials of plastic form which become flexible and can be molded into different shape when heated to a temperature of 50 to 60 degrees C., and will become rigid and nondistensible when the temperature is lower, generally to room temperature 20 to 30 degrees C. Such materials are available commercially in the United States, such as the Orthoplast used in orthopedics.

Generally, any space that exists between the cuff and the surrounded body except that occupied by the balloon is known as dead space, as is any unnecessary volume due to excessive lengths of piping or other fluid conduit between the inflation/deflation valves and the balloon inflation devices. It is essential to reduce this dead space as much as possible so that the least amount of energy in the form of compressed air is required to inflate the balloons to the required pressure in the quickest way. This will reduce the size and energy consumption of the compressor, reduce noise level and therefore reduce the total size of the external counterpulsation apparatus.

To achieve the object of closely fitting the body and reducing the dead space, proper paddings 43 can be provided between the balloons and the balloon cuffs. The paddings may be bags of unformed materials (such as water, powder, fine sand, etc.) or triangular pads made of formed materials (e.g. rubber), the former could form a pressure bearing surface which fits the contour of the pressure bearing portion of the body when it bears pressure; while the latter could meet the needs of patients of various bodily forms by simply moving the paddings upward or downward to avoid the need to provide balloon cuffs of various sizes. To prevent the skin of a patient from being chaffed as a result of vibrations produced during counterpulsation, the edges of the balloon cuff body should be smoothed, this could be done by slightly turning the edges outwardly, and also could be done by wrapping the edges with soft materials (e.g. cloth, sponge, etc.). The balloon cuff body could be made from a single piece of material, but for convenient operation, it is preferable that it be fabricated in separated pieces which are coupled together with hinges 42 to enable freely opening and closing.

A balloon cuff body of proper size is selected or fitting paddings are inserted into the balloon cuff to fit the bodily form of the patient to make the balloon cuff closely encircle the corresponding portion of the patient. Fixing belts 45 are then tightened, and counterpulsation can begin.

Another way to reduce such dead space and its "dash pot" effects on the system is to locate the inflation/deflation valves as close as possible to the balloon inflatable devices, such as on or under the patient treatment table itself, for example.

Figure 7:
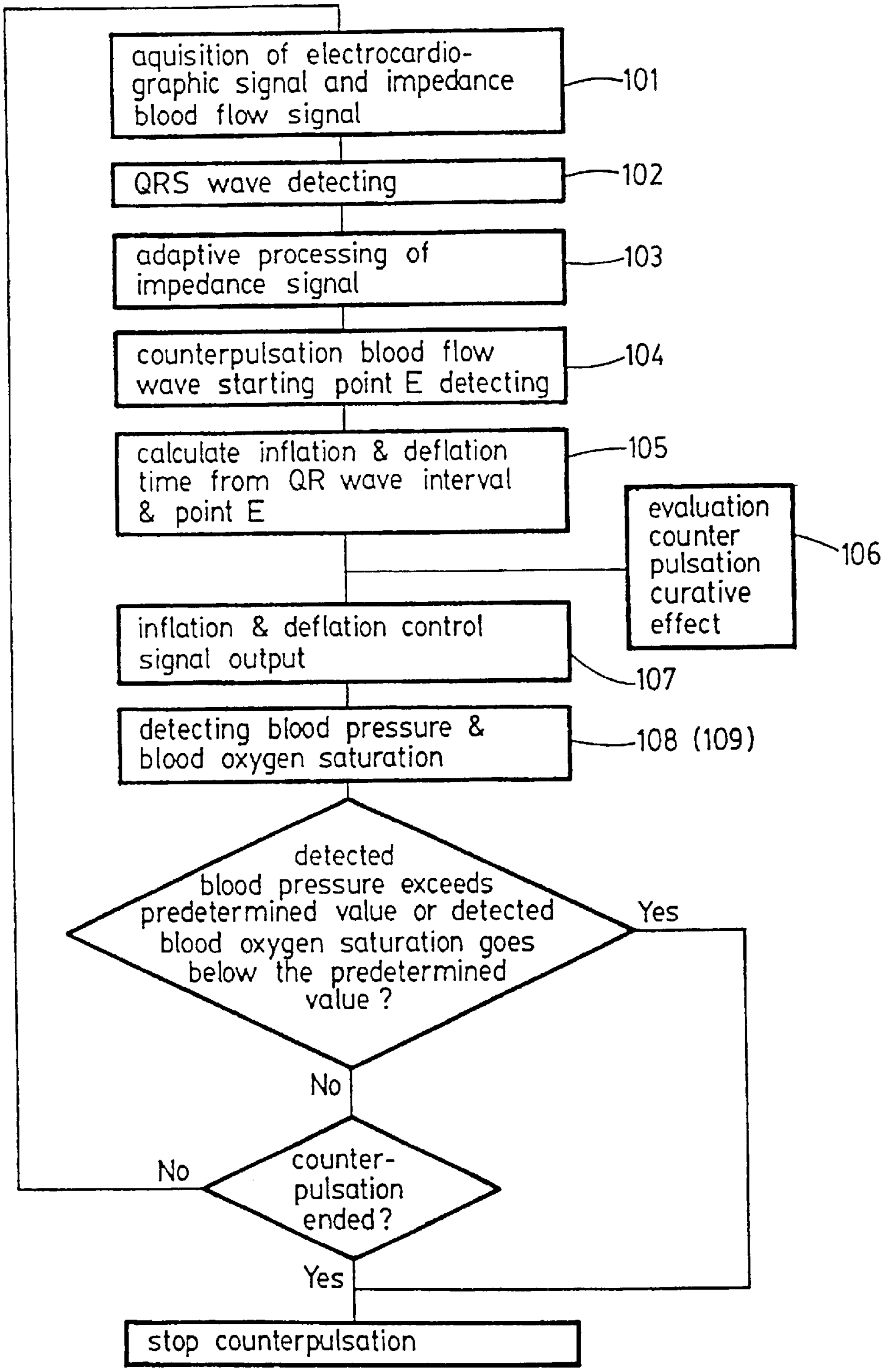
FIG. 7 is a flow chart of the method for controlling the external counterpulsation apparatus according to the present invention.

FIG. 7 is a flow chart of one control method of the external counterpulsation apparatus according to the present invention, which comprises the steps of: a). obtaining an impedance cardiograph and electrocardiographic signals having a clear and stable wave form in the counterpulsation state by the use of detector electrodes 1, high frequency constant current source 2, and electrocardiographic and impedance signal amplifier-filter means 3, 4 and 5, which are collected and displayed by the computer system 7 (101); b), the computer system detecting the QRS wave of the electrocardiographic signal (102), performing adaptive processing of the impedance blood flow signal (103), obtaining the starting point of the counterpulsation blood flow wave by detecting the impedance cardiograph after self adaptive filtering processing (104), and calculating the data for controlling the inflation and deflation time of the counterpulsation apparatus from the interval of the R wave of the electrocardiographic signal and the starting point of the counterpulsing blood flow wave (105); c), obtaining an objective index reflecting the curative effect of counterpulsation by detecting the peak amplitude of the waveform and duration of the heart systolic wave and counterpulsing wave in the impedance cardiograph (106); and d), controlling the inflation and deflation of the external counterpulsation apparatus by the computer (107). For the safety of the patient during counterpulsation, the control method of the present invention further comprises the following steps; e), detecting the blood pressure state of the patient with a blood pressure detector means during counterpulsation (108); and f), detecting the oxygen saturation of the blood of the patient with a blood oxygen detector during counterpulsation (109). If the detected blood pressure value exceeds a predetermined value, or the blood oxygen saturation goes below a predetermined value, then the computer will direct the apparatus to stop counterpulsation.

Possible serious complications from external counterpulsation treatment include pulmonary edema and cerebral hemorrhage. Pulmonary edema may arise because of left ventricular (left heart) failure, and usually can be detected with a rapid drop in the oxygen saturation of the arterial blood, from a normal value of 95–98% to a value lower than 85–90%. The monitor of oxygen saturation is an extremely sensitive parameter for the detection of pulmonary congestion due to left heart failure. The oxygen saturation can be monitored with a pulse oximeter available commercially and commonly used in any operating room. The use of pulse oximetry as a noninvasive method to detect the complications of pulmonary congestion (edema) as well as left heart failure is a novel concept provided in the present invention. Furthermore, cerebral hemorrhage usually results from high arterial blood pressure (hypertension). Since an effective external counterpulsion can raise the peak diastolic pressure to 40 to 60 mm Hg above systolic blood pressure, it is important not only to measure the resting blood pressure of patient before initiation of external counterpulsation (so that hypertension patients can be treated medically to reduce their blood pressure before counterpulsation treatment), but it is also important to monitor the peak arterial blood pressure during treatment to ensure the peak blood pressure will not rise more than 40 to 50 mm Hg above resting systolic pressure. The present invention provides a novel means to monitor the peak blood pressure effectively. Historically, it is extremely difficult to measure blood pressure using any of the presently available measuring methods during external counterpulsation because of motion artifact as well as the noisy environment. The present invention provides a means to accurately determine the peak blood pressure, thereby producing a critical parameter in eliminating such dangerous complication as cerebral hemorrhage.

A closed loop control procedure is performed by the computer and is as follows: At the beginning of the counterpulsation, the computer automatically sets the balloon inflation time to be at the end of the T wave of the electrocardiograph. Due to the delay before the arrival of the counterpulsing wave at the aorta, the closing point of the aortic valve and the starting point of the counterpulsing wave can be detected from the heart impedance blood flow graph by the computer. The computer adjusts the inflation time of the counterpulsation apparatus according to the time difference between these two points to move the starting point of the counterpulsing wave gradually towards the closing point of the aorta. While gradually matching of these two points, the computer also calculates the aorta closing time with the Bazett formula ($T_{QT}=K\surd T_{RR}$) because of the effect of counterpulsation on the automatic detecting of the closing point of the aorta. The time QT calculated with the Bazett formula is taken as the closing time of the aorta valve after the Q wave of the electrocardiograph has been detected. This makes the starting point of the counterpulsing wave fall into a range centered at the closing time of the aortic valve. In the procedure of gradually matching the two points, the detection of the starting point of the counterpulsing wave may be affected by blood expulsion from the heart and the variation of blood flow inside the chest. If so, the computer determines the time delay between the arrival of the counterpulsing wave at the central region of the aorta and its formation by the pressurization of the lower limbs of the patient, by determining the time difference between the detected starting point of the counterpulsing wave and the inflation time. The computer adjusts the counterpulsation inflation time, such that the starting point of the counterpulsation formed after the time delay falls into a range centered at the closing time of the aortic valve. The computer keeps it in this range during counterpulsation, thereby, performing loop control.

Figure 8:
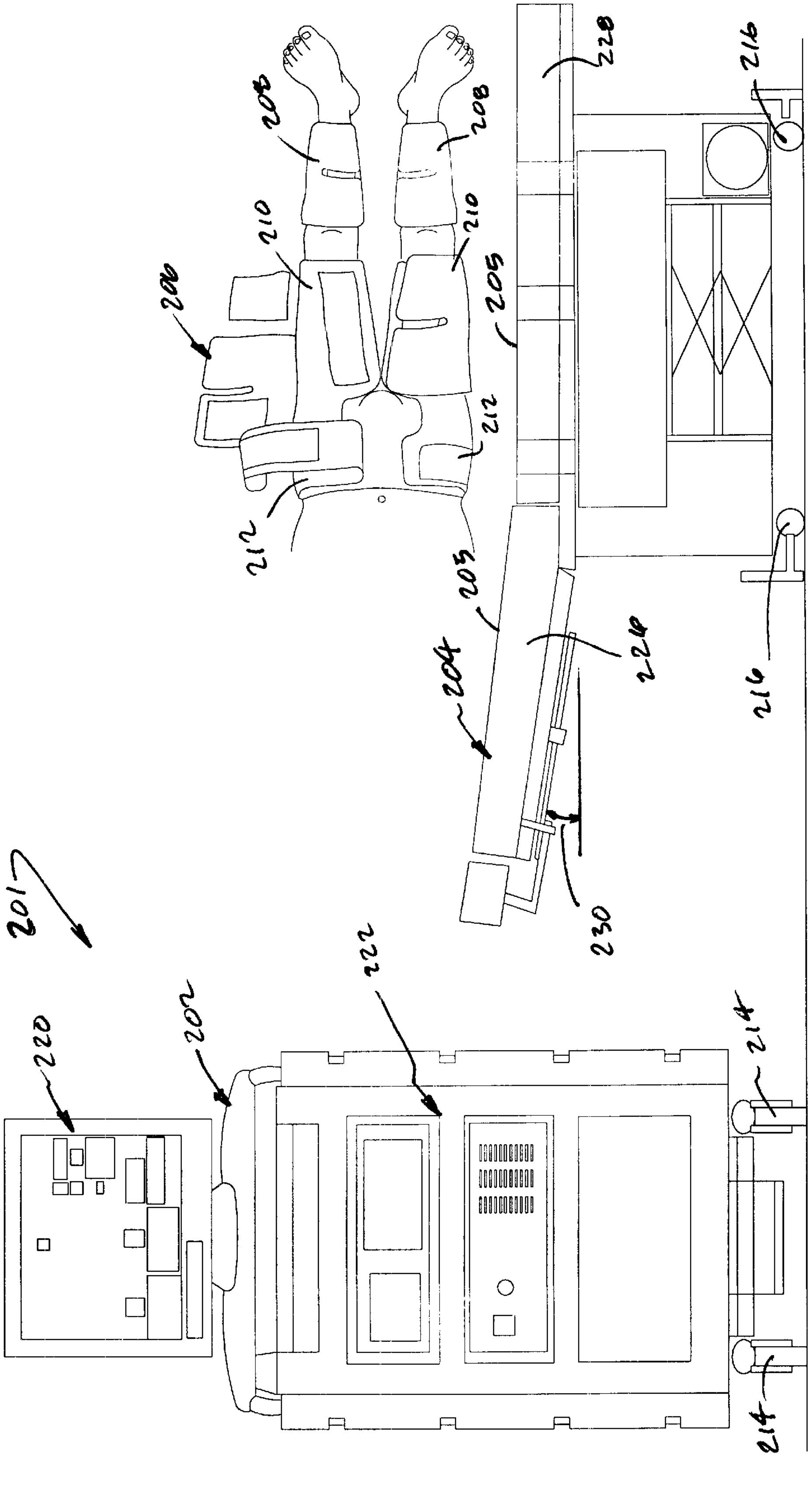
FIG. 8 is a diagrammatic view of an improved external counterpulsation apparatus according to the present invention.

Beginning with FIG. 8, a further improved external counterpulsation apparatus 201 is illustrated and described. The external counterpulsation apparatus 201 includes three basic component assemblies, namely a control console assembly 202, a treatment table assembly 204, and a balloon inflation/deflation assembly 206. The control console assembly 202 is mounted for mobility from one location to another upon wheels 214, and similarly the treatment table assembly 204 is mounted for mobility from one location to another upon wheels 216. As used herein the term “wheels” includes casters, rollers, track-type belts, or other lockable and unlockable wheel-type devices configured for allowing the components to be “wheeled” from one location to another and then locked in order to maintain the desired position or location. The control console assembly 202 generally includes a user interface device, such as a computer monitor or touch screen 220, and a cabinet or housing 222, in which various components described below are located and housed.

The treatment table assembly 204 generally includes an upper surface 205 on an articulatable portion 226 and a horizontal portion 228, with the articulatable portion 226 being hingedly or otherwise pivotally interconnected with the horizontal portion 228 for adjustment (either manually or by way of a power drive) to a plurality of angulated positions relative to the main horizontal portion. In this regard, it should be noted that the angulated position of the articulatable portion relative to the main horizontal portion is preferably limited to an angle 230 that is 30 degrees above the horizontal. Thus, by way of the motor-driven elevation assembly 224 and the articulatable portion 226 of the treatment table assembly 204, a patient receiving treatment can be easily positioned or situated on the upper surface 205, elevated to a desired working height, and made comfortable by angulation of the articulatable portion 226 relative to the horizontal main portion 228. In this regard, it should be noted that the motor-driven elevation assembly 224 preferably includes a limiting switch or other limiting device (not shown) that limits the elevation of the top or upper surface of the horizontal main portion 228 of the treatment table between heights of 24 inches and 36 inches from the floor or other surface upon which the treatment table assembly 204 is situated.

Figure 9:
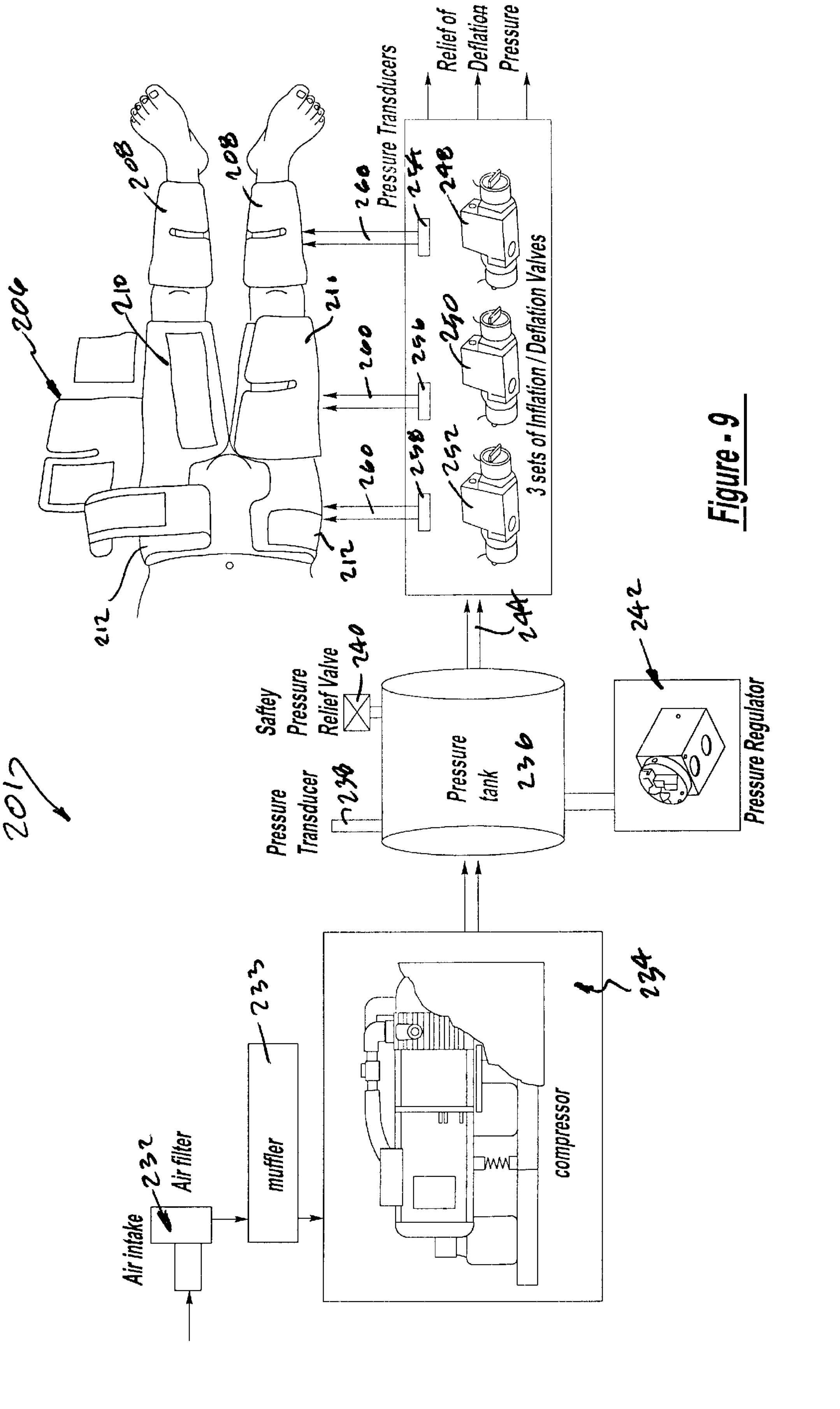
FIG. 9 is a diagrammatic representation of the air flow of the external counterpulsation apparatus of FIG. 8.
Figure 10:
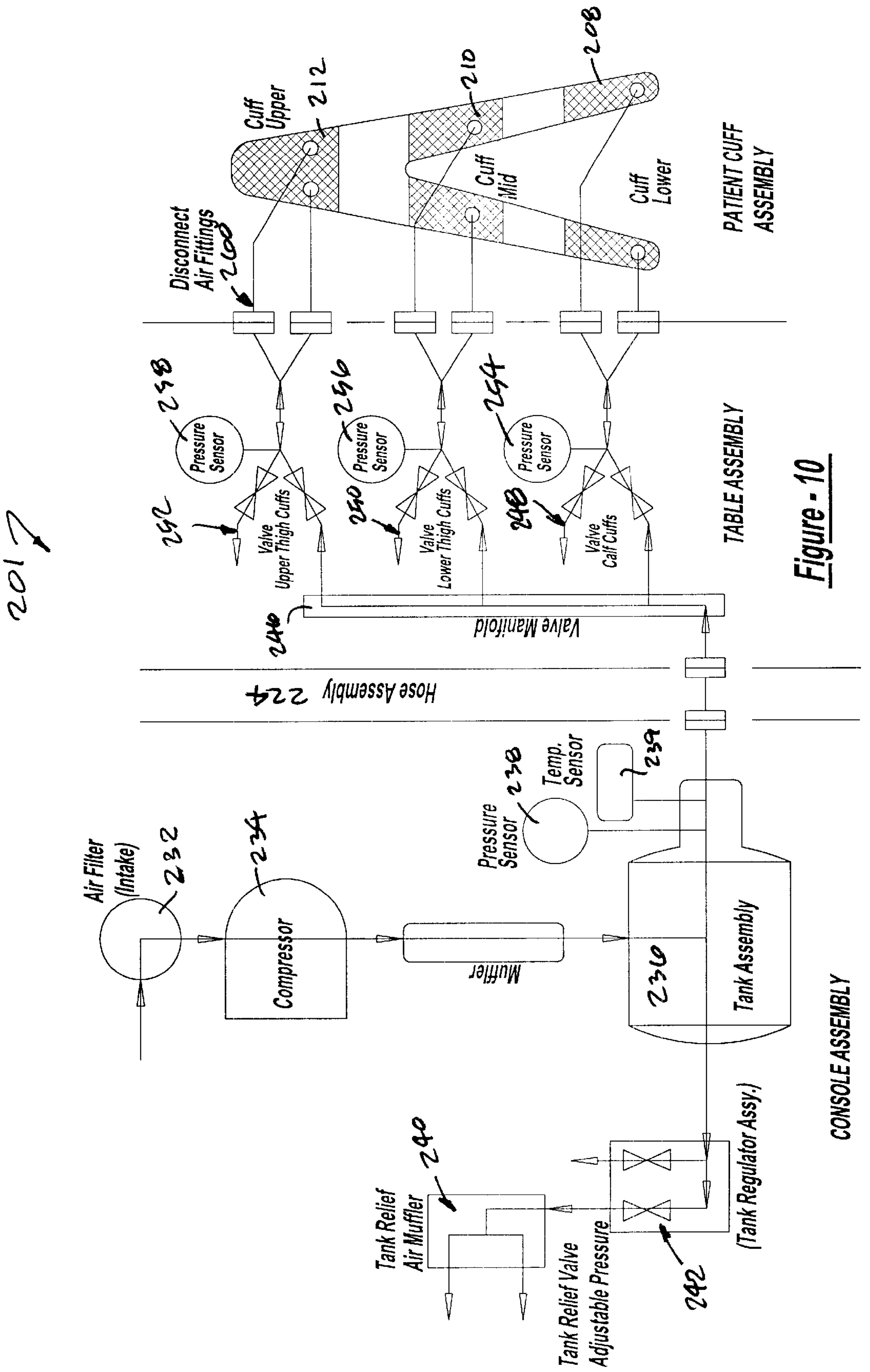
FIG. 10 is a flow diagram similar to that of FIG. 9, but illustrating minor variations thereon.

FIGS. 9 and 10 are schematic or diagrammatic representations of the compressed gas (preferably compressed air) flow arrangement for the external counterpulsation apparatus 201. The apparatus 201 preferably includes an air intake/filter assembly 232, a muffler 233, which can be located before or after a compressor 234, as shown in contrast in FIGS. 9 and 10, a pressure tank 236, a pressure sensor/transducer assembly 238, a pressure safety relief valve 240, and a pressure regulator 242. A temperature sensor 239 is also preferably included, as shown in FIG. 10. All of these components are preferably housed within the cabinet or housing 222 of the control console assembly 202.

A hose connection assembly 244 is used for quick connecting and disconnecting the above-described components with those mounted on, or otherwise associated with, the treatment table assembly 204. Such treatment table assembly components include a valve manifold 246, as shown in FIG. 10, a number of sequentially operable inflation/deflation valves 248, 250 and 252, each with an associated pressure transducer/sensor 254, 256, and 258, respectively. A connect/disconnect assembly 260 is provided for quick and easy connection and disconnection of the inflation/deflation valves 248, 250 and 252 with their associated inflatable cuff devices 208, 210, and 212, respectively, of the balloon assembly 206.

FIG. 11 diagrammatically illustrates the electrical/logic/control interconnections of the various components of the external counterpulsation apparatus 201. The control console assembly 202 includes a power supply 264 that feed power to a computer CPU assembly 219, which includes the above-mentioned user interface monitor 220, as well as other input and keyboard provisions, as well as to the compressor assembly 234, by way of a power converter and ramp-up assembly 266. The converter and ramp-up assembly converts electrical power to the compressor from 110/120 VAC 50/60 hz to three-phase 220 VAC at a variable frequency and increases the electrical power to a preselected full power level over a period preferably of approximately three to approximately five seconds. At the onset of external counterpulsation treatment for the patient, electrical power is required to power the three sets of inflation/deflation valves, as well as to provide the base line requirement of electrical energy to the computer CPU assembly 219, the user interface monitor 220, and other electronics associated with the external counterpulsation apparatus 201. This can result in a power surge of up to or even exceeding 30 amperes. This power requirement is too high for most normal house power supply systems. Therefore, the power converter and ramp-up assembly 266 includes a variable frequency drive transistorized inverter (e.g., Mitsubishi Model FR-E520-1.5K) to slowly ramp up the power supply to the compressor over the above-mentioned preferred period of approximately three to approximately five seconds. The power converter and ramp-up assembly 266 converts 110/220 VAC 50/60 hz line input and converts it to three-phase 220 VAC and with variable frequencies, starting at 0 hz and up to a preset frequency (e.g., 72 hz). Thus, the operation of the compressor assembly 234 is independent of the input line's frequency, and there is no sudden power surge required to start the compressor. This "soft start" has not been found to affect the operation of the external counterpulsation apparatus 201 in either effectiveness or safety.

In terms of user friendliness, various related functions of the system 201 are grouped for easy and logical operation. All patient-related inputs (patient ECG, finger plethysmography, patient call button, etc.) are located in one location, namely on the treatment table assembly 204. Outputs, such as printer outputs, patient signals, outputs, service signals, outputs, etc., are also grouped in one location, preferably on the control console assembly 202. Operator inputs for purposes of adjusting performance of the apparatus 201, are all on the touch screen display of the user interface monitor 220, and include inflation/deflation timings, magnitude of pressure applied, and other important data discussed below, including the display of the patient's ECG, graphic representations of the inflation/deflation timings, finger plethysmogram for monitoring appropriate timing adjustment and other operational factors.

Figure 12:
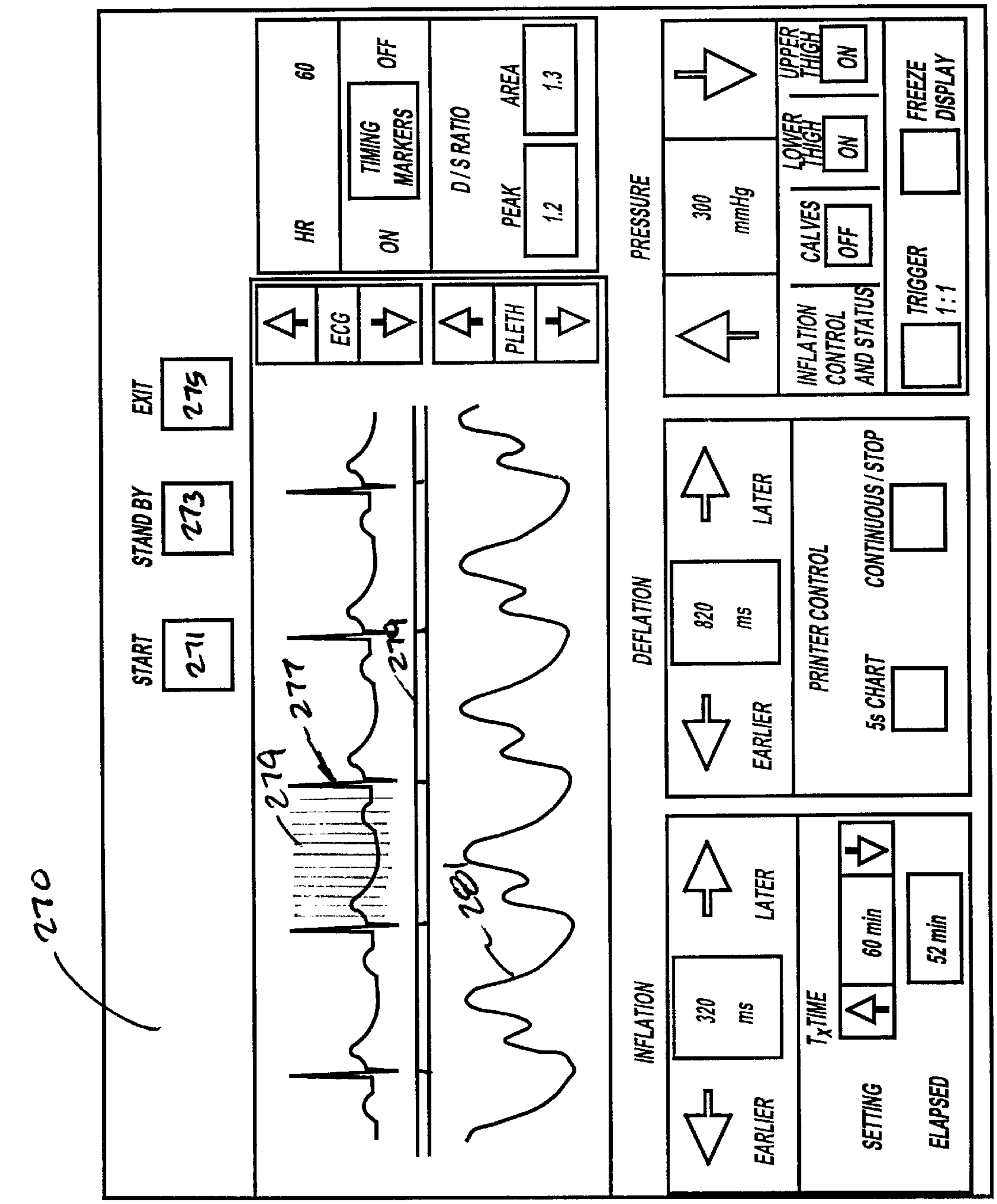
FIG. 12 is an illustration of a user interface screen or monitor for use in the present invention.

As is mentioned or described in detail below, the user interface monitor display 220 is preferably a touch screen for easy monitoring of patient treatment status, treatment parameters, and other relevant data, and provides the capability for adjustment to control operation. As shown in FIG. 12, the user interface monitor or touch screen display 220 includes patient data 270 in the upper left hand portion of the display, which is in communication with the patient's data base allowing an operator to create a patient file for each new patient and allowing the system or apparatus 201 to track the accumulated treatment time for proper dosage for the patient.

Ease of initiation and termination of operation is accomplished with three buttons on the top line of the display, namely a start button 271 for initiation and continuation of treatment, a standby button 273 which can be used to place the external counterpulsation apparatus 201 on "hold", whenever the patient needs to rest, use a restroom, or otherwise temporarily pause the treatment, and to then resume when the patient returns to complete the treatment session. In this regard, the treatment timing function would not run during this pause time, thus allowing it to keep track of total effective treatment time. An exit button 275 is provided to stop the treatment session for a particular patient and to record the elapsed treatment time in the patient data base for use in future treatment sessions.

An ECG display 277 is included with timing markers and bars 279 superimposed on or adjacent the ECG signal for easy identification of inflation and deflation timing, which is illustrated by the graphic inflation/deflation display 281. The timing markers are equal amplitude signals that may not be misinterpreted as noise, and can be turned "on" or "off" for proper identification of the ECG signals. The timing bars also identify the trigger signals (to be checked against the ECG's R-wave), as well as the inflation and deflation times, which demonstrate the period of the cardiac cycle when external pressure is applied. This enables operators to easily identify and verify that they are not inflating the cuffs during the cardiac systole when the heart is pumping or ejecting blood. The user interface monitor 220 also includes digital display of inflation and deflation time, digital display of the magnitude of external pressure applied to the patient, digital display of the intended treatment period for this patient during the current session, which can be increased or decreased digitally, with the default preferably being a treatment of 60 minutes. Digital display of the elapsed treatment time is also provided and the three pairs of inflation/deflation cuff devices can individually be turned "on" or "off", which condition is easily identified and displayed in the lower right hand of the display screen.

Figure 13B:
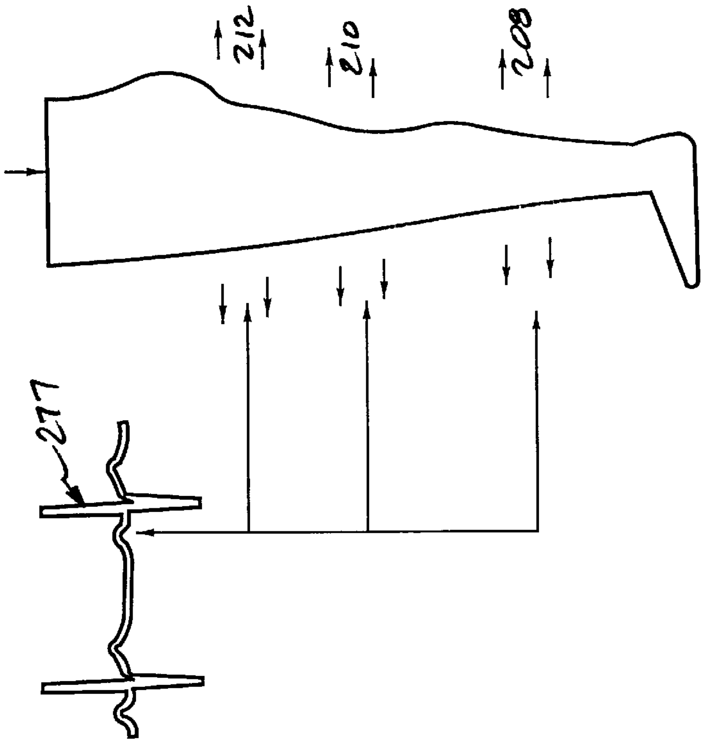
FIGS. 13A and 13B are diagrammatic representations of the inflation and deflation of inflatable cuff devices of the present invention for use in treatment of a patient, coordinated with the associated portions of the patient's ECG.
Figure 13A:
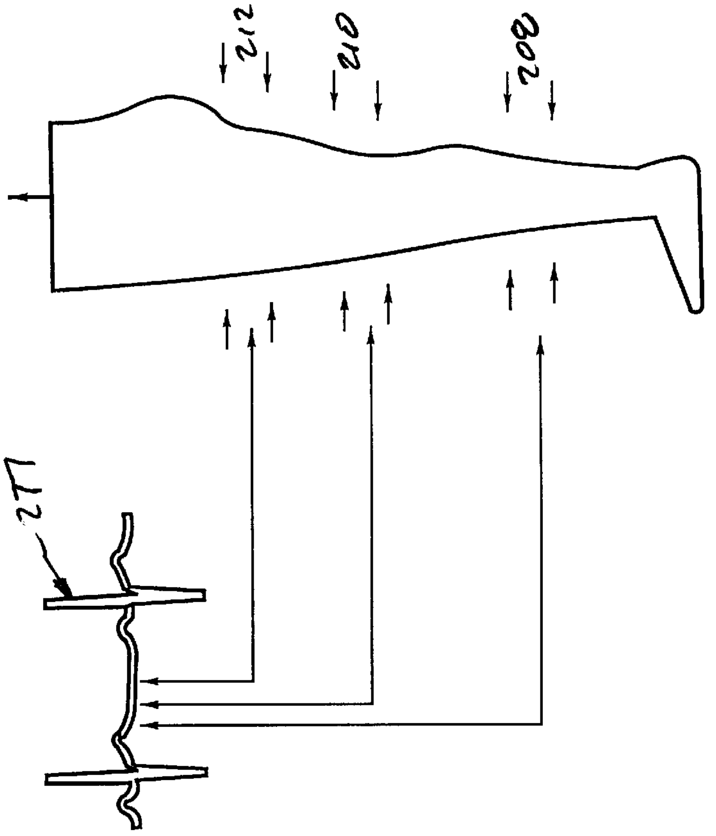
Figure 14:
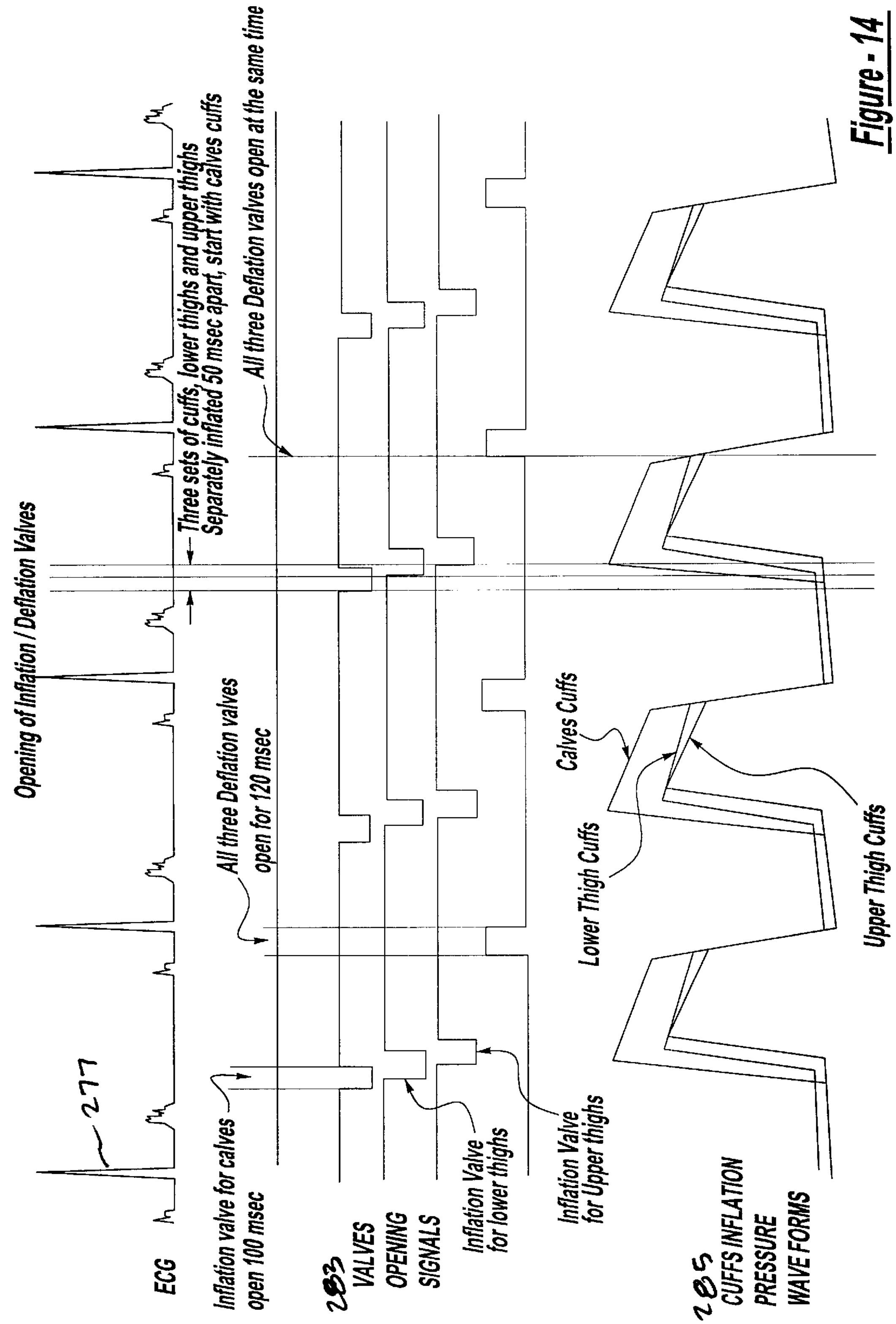
FIG. 14 is a graphic representation of the relationship between the patient's ECG, the valve opening signals and the inflatable cuff device inflation pressure waveforms during operation of the external counterpulsation apparatus of FIGS. 8 through 13.
Figures 15A, 15B:
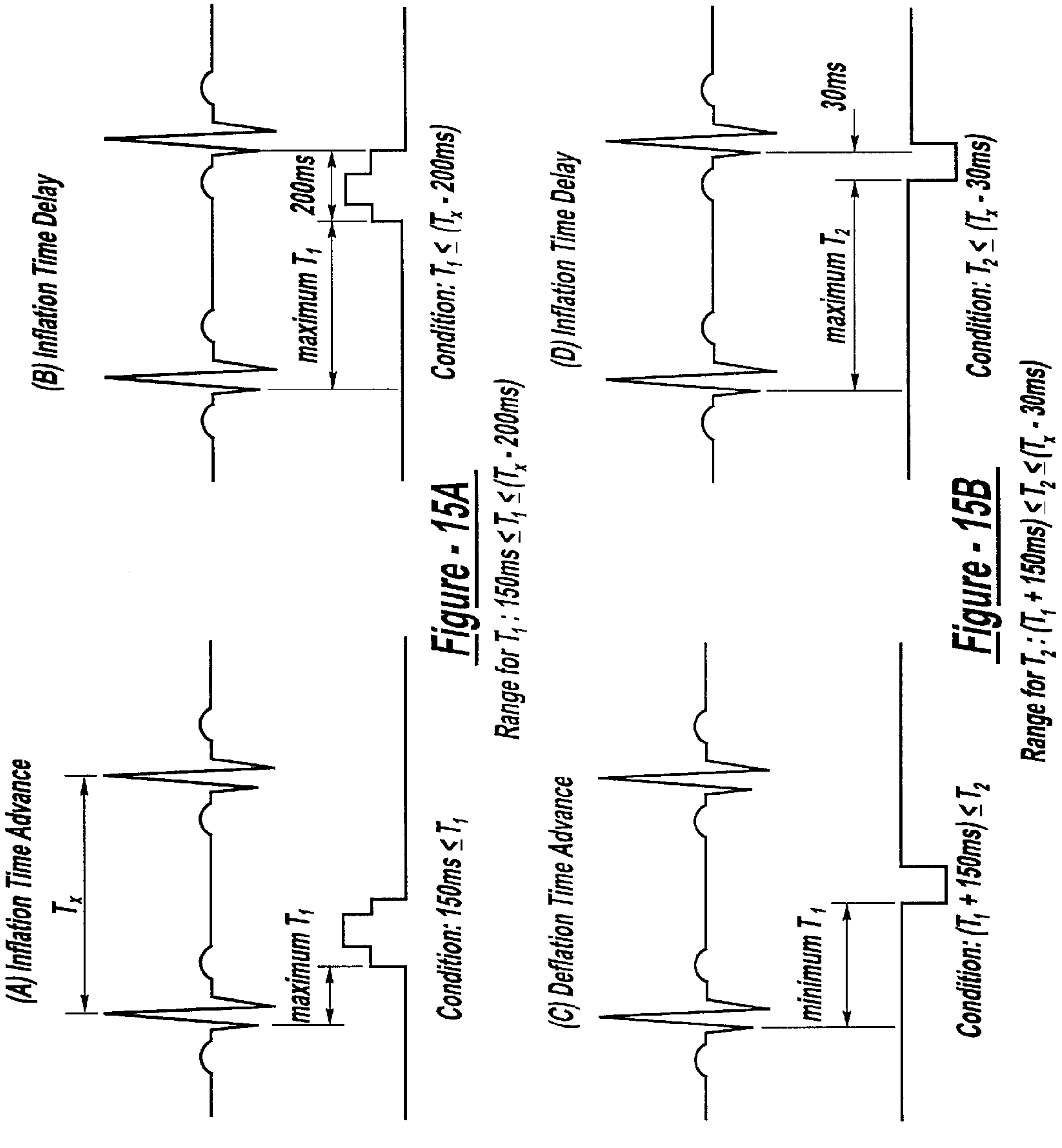
FIGS. 15A and 15B are graphic representations of possible inflation time advances and delays and possible deflation time advances and delays.
Figure 16:
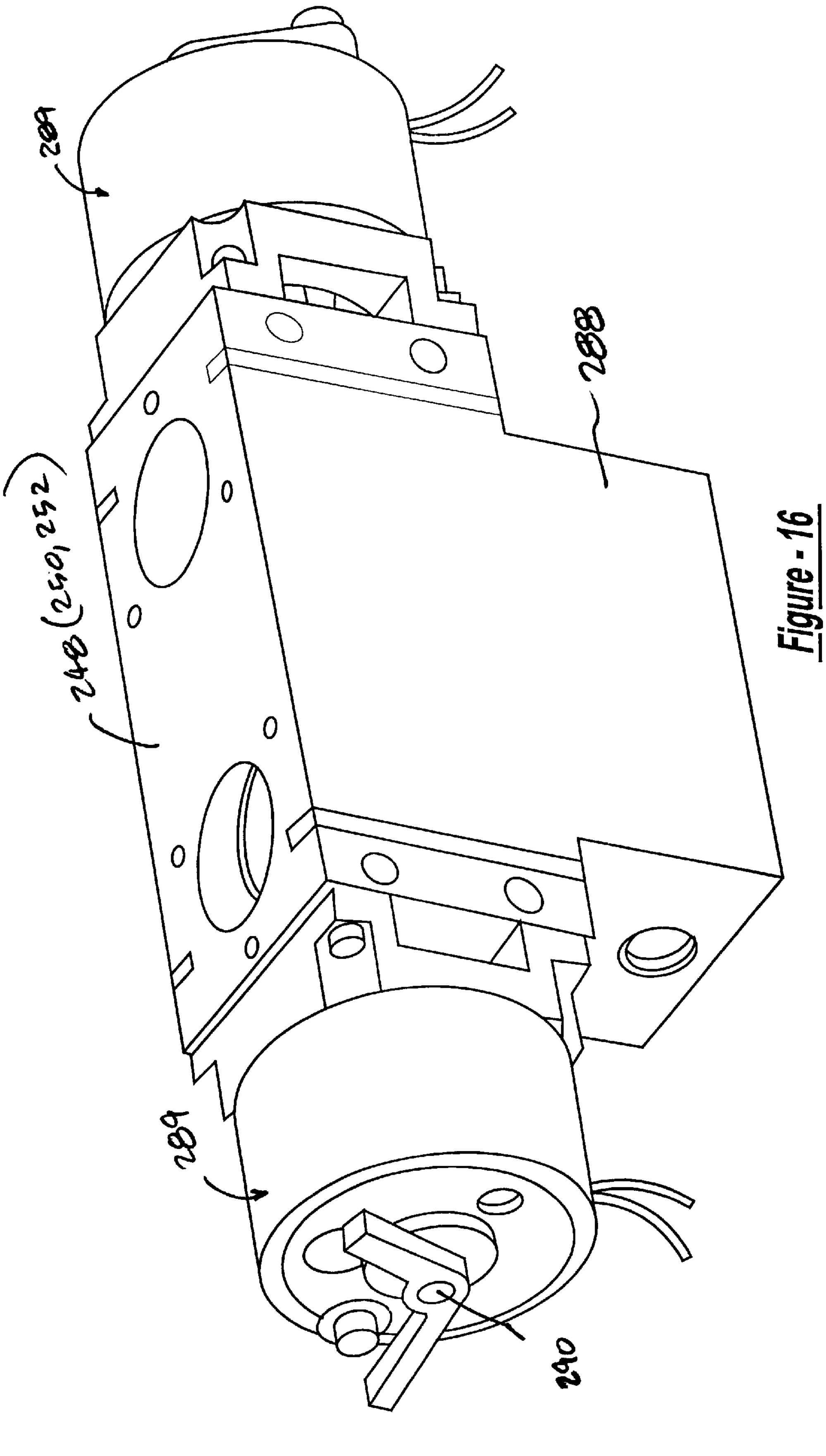
FIGS. 16 through 22 illustrate an exemplary inflation/deflation valve for use in an improved external counterpulsation apparatus according to the present invention.
Figure 19:
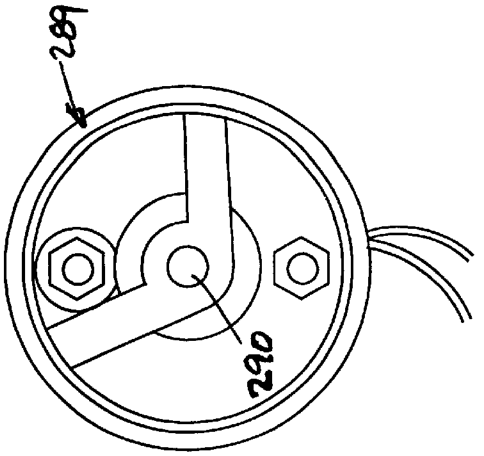
Figure 17:
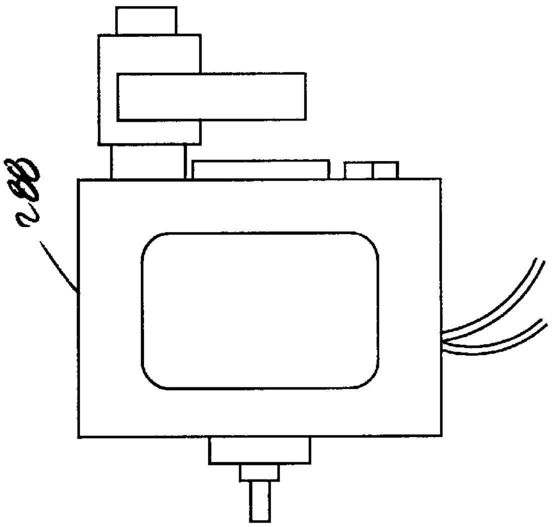
Figure 18:
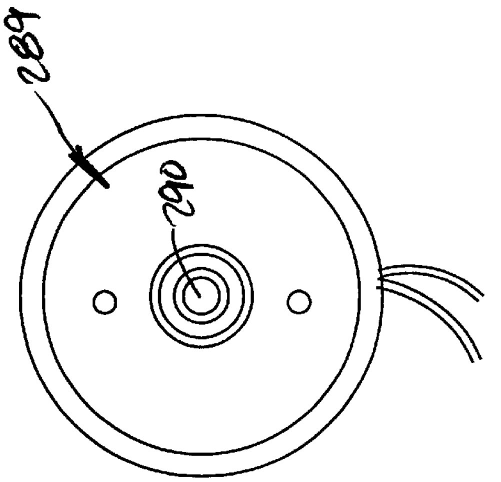
Figure 20:
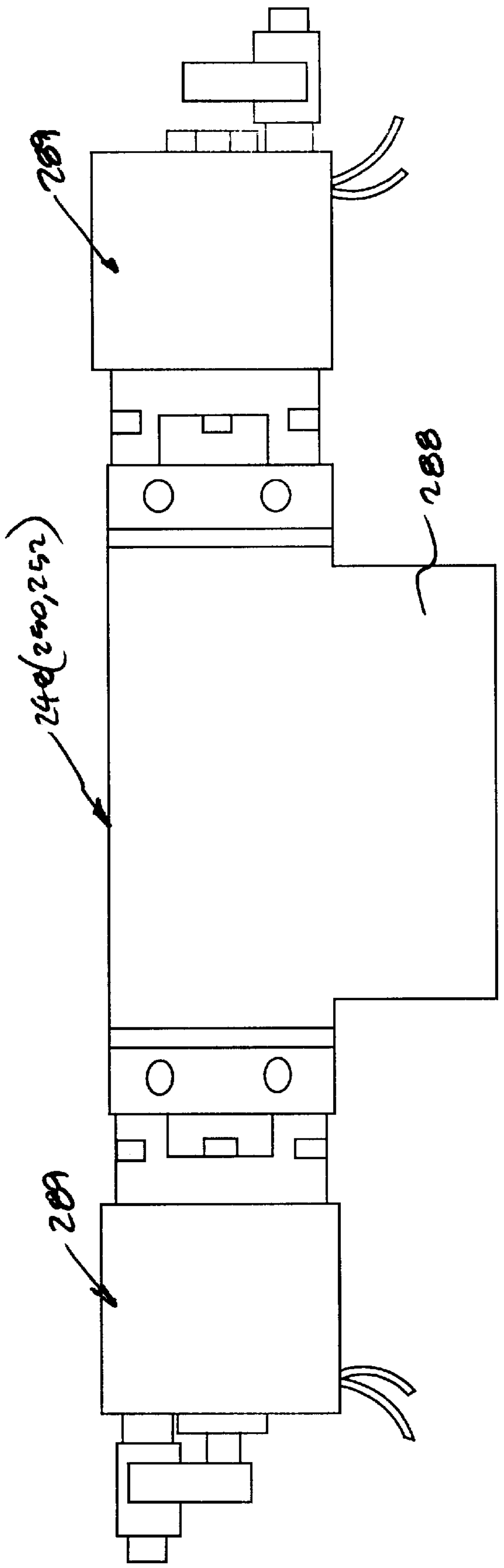
Figure 21:
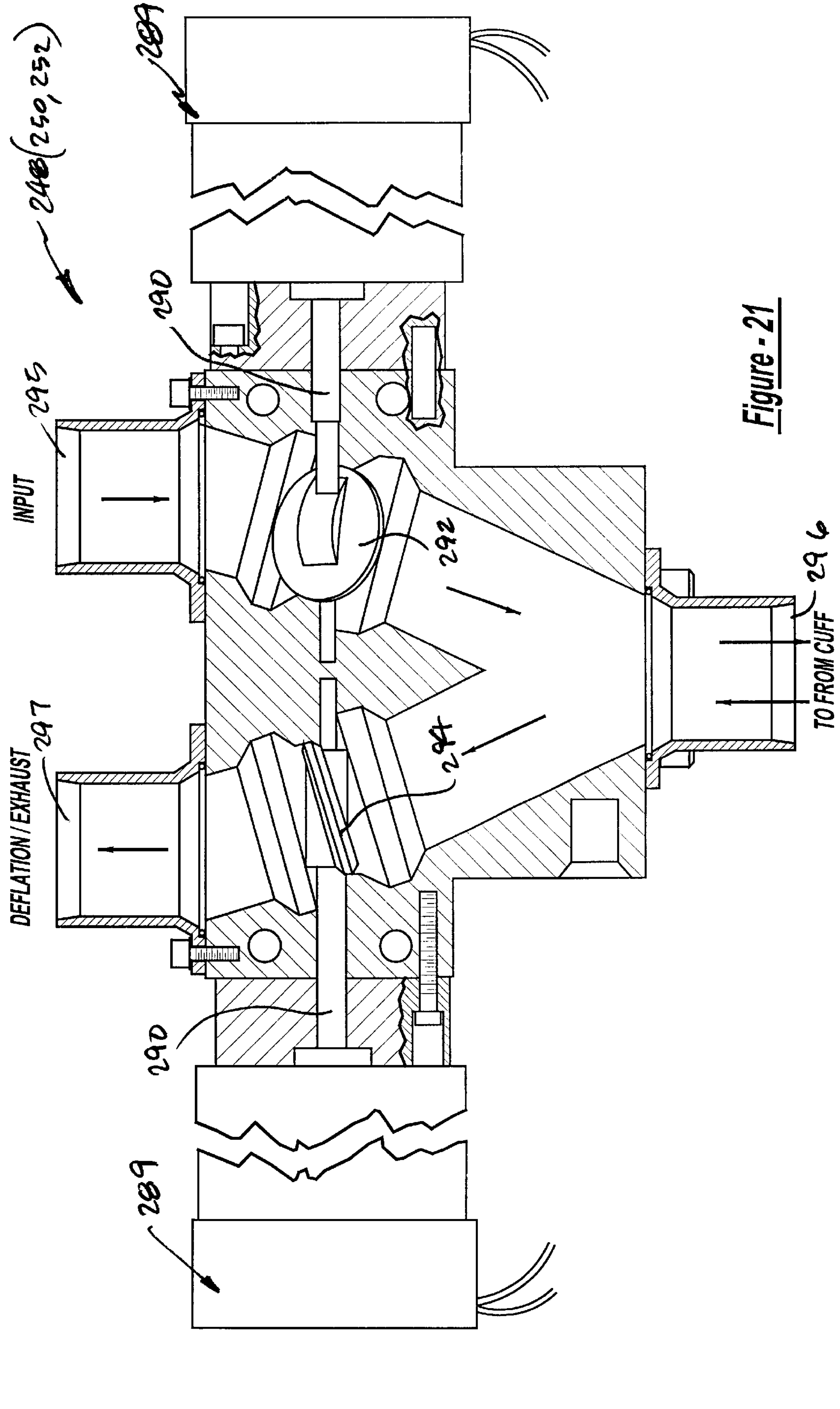

All of the above-described controls and features are configured and calculated to provide for sequential pressurization of the patient's lower limbs, beginning at the most distal area at which the inflation cuff device 208 is applied, followed by the medial area at which the inflatable cuff device 210 is positioned, and ending with the pressurization by the inflatable cuff device 212 at the upper end of the patient's leg or the buttock area. This sequence is indicated graphically in FIGS. 13A and 13B, with the exhausting of all pressure to the inflatable cuff devices 208, 210 and 212 occurring near the end of the ECG cycle, as illustrated in FIG. 13B. This relationship is also graphically illustrated in FIG. 14, which juxtaposes the ECG signal 277, the valve opening signals 283 and the inflatable cuff device pressure waveforms 285. As illustrated in FIGS. 15A and 15B, the inflation time can be advanced or delayed by the operator between certain minimums and maximums.

FIGS. 16 through 22 illustrate an exemplary inflation/deflation valve 248, which should be regarded as typical for the inflation/deflation valve 250 and 252 as well. The inflation/deflation valve 248 (and 250 and 252) is preferably a rotary actuable butterfly-type valve, which can be actuated pneumatically or in the preferred embodiment electrically by the respective operators 289 on opposite ends of a body portion 288 for controlling the rotatable rotors 290. Attached to the rotors 290 are butterfly valve elements 292 and 294 which open and close the compressed gas or compressed air inlet 295 and the inflation/deflation port 296, which is connected to the respective or associated inflatable cuff devices 208, 210, or 212, with the butterfly valve element 294 being rotatable actuable to open and close fluid communication between the inflation/deflation port 296 and a deflation exhaust port 297. The quick-acting operators 290 are respectively actuated and controlled by way of the control system described herein, in order to provide for proper inflation and deflation timing and sequential operation of the inflatable cuff devices 208, 210, and 212. The butterfly valve elements and their associated rotors 290 are preferably rotatable through a maximum rotation angle of approximately 60 degrees between open and closed positions.

Preferably the inflation passageway through each of the butterfly valve openings between the input port and the inflation/deflation port is somewhat more restricted than the deflation passageway between the inflation/deflation port and the deflation exhaust port, with the restriction being approximately 20 to 30 percent larger on the deflation side than on the inflation side in order to allow deflation of the inflatable cuff devices at the same rate as the inflation rate, owing to the fact that the inflation has a higher pressure gradient between the compressed gas or air at the input 295 and the inflation/deflation port 296 when compared with the pressure gradient between the inflation port 296 and the deflation exhaust port 297.

Preferably, the butterfly valve elements 292 and 294, along with their associated rotors 290 are driven by a rotary solenoid using fifteen volt DC continuous power or twenty-seven volt DC fifty msec pulse, dropping back to a fifteen volt holding voltage. This lower power consumption is important not only to reduce the overall electrical power requirement, but to reduce the heat output.

For safety and other quick-acting purposes, the deflation butterfly valve element 294 is normally open (such as in a power-off condition) and the inflation butterfly valve element 292 is normally closed. Thus, in the case of a power loss, the inflation valve element 292 will be closed and the deflation valve element 294 will open to allow air from the inflatable cuff devices to deflate and exhaust to atmospheric pressure.

Each of the butterfly valve elements 292 and 294 preferably open from one hundred msec to two hundred msec to allow compressed air from the above-mentioned reservoir to be admitted to the inflatable cuff devices during the onset of a diastole. As mentioned above, the timing and opening times of the inflation valves are variable in order to correctly correspond with the patient's heart rate, but preferably not less than one hundred msec duration. At the end of a diastole, the deflation butterfly valve element 294 opens (even without electrical power) for a period of one hundred twenty to one hundred twenty msec. It is desirable to make the period of opening of the deflation butterfly valve element 294 variable according to the heart rate, but with an opening time of not less than one hundred twenty msec during normal operation. It should be noted that it would be possible to use three-way valves, as an option. However, it is important to be assured that there will be no cross-overleakage, if such three-way valves are used, when switching from the inflation port to the deflation port and vice versa.

Figure 23:
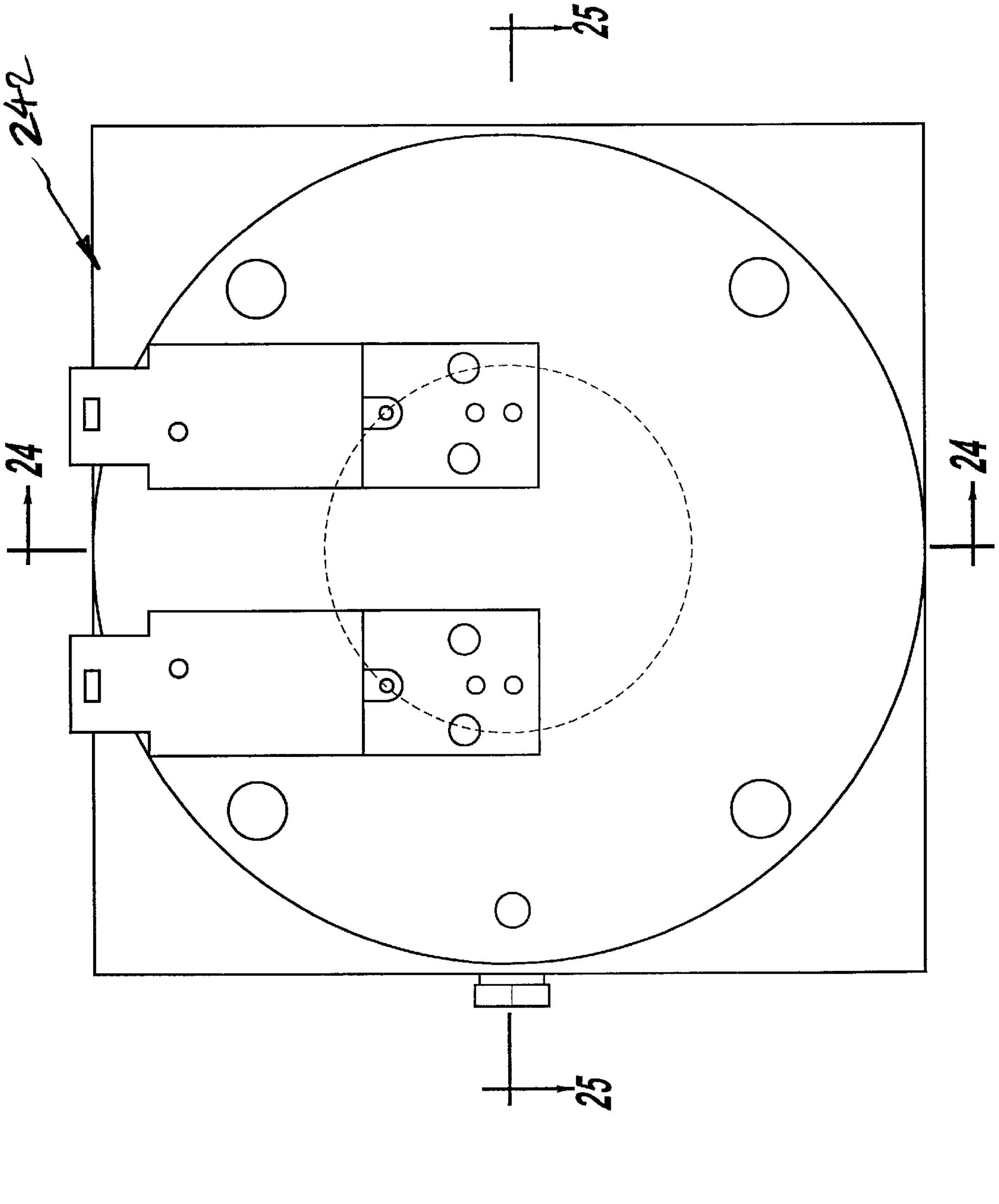
FIGS. 23 through 25 illustrate a pressure regulator assembly for use in the external counterpulsation apparatus of FIGS. 1 through 22.
Figure 24:
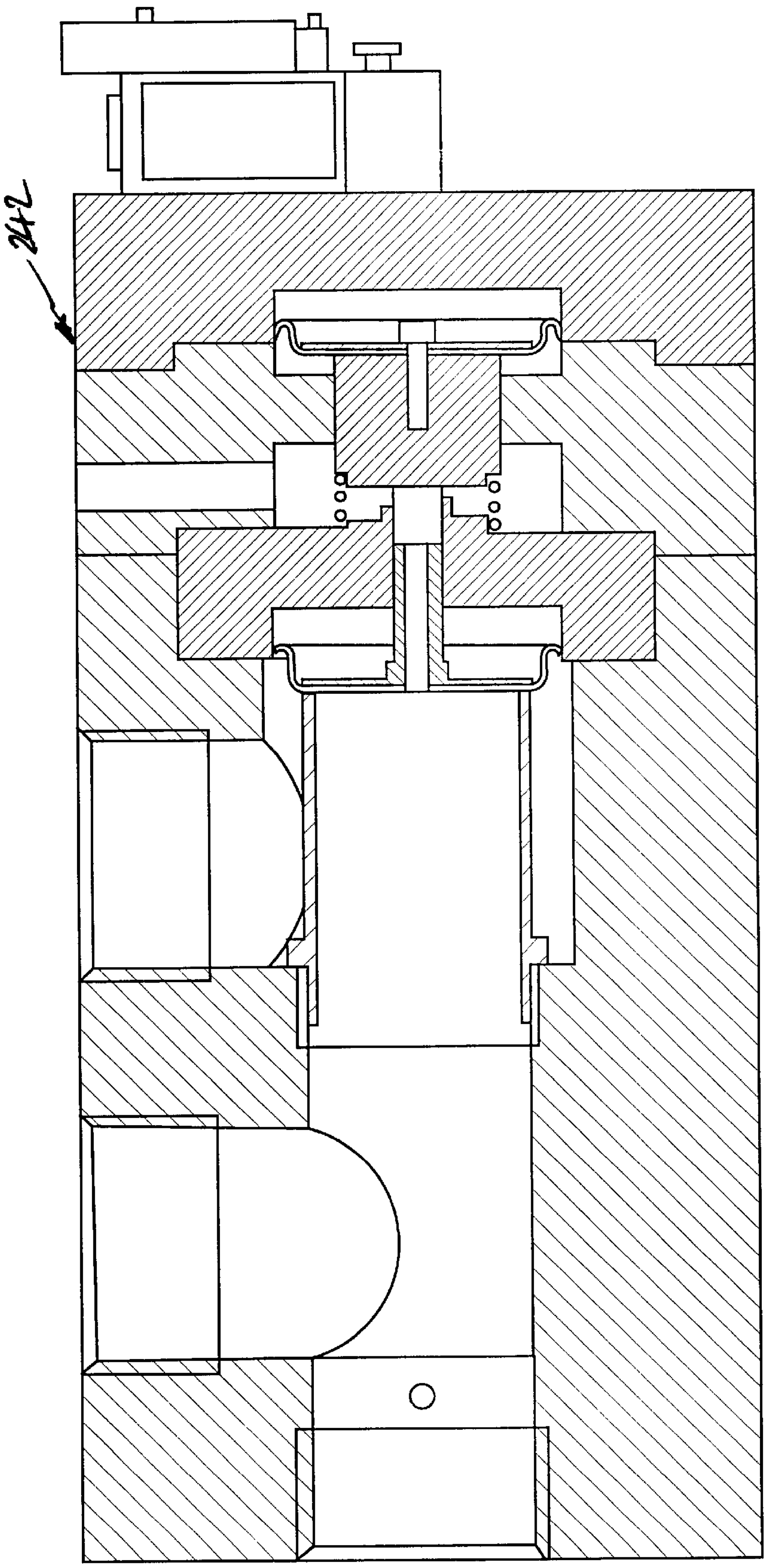
Figure 25:
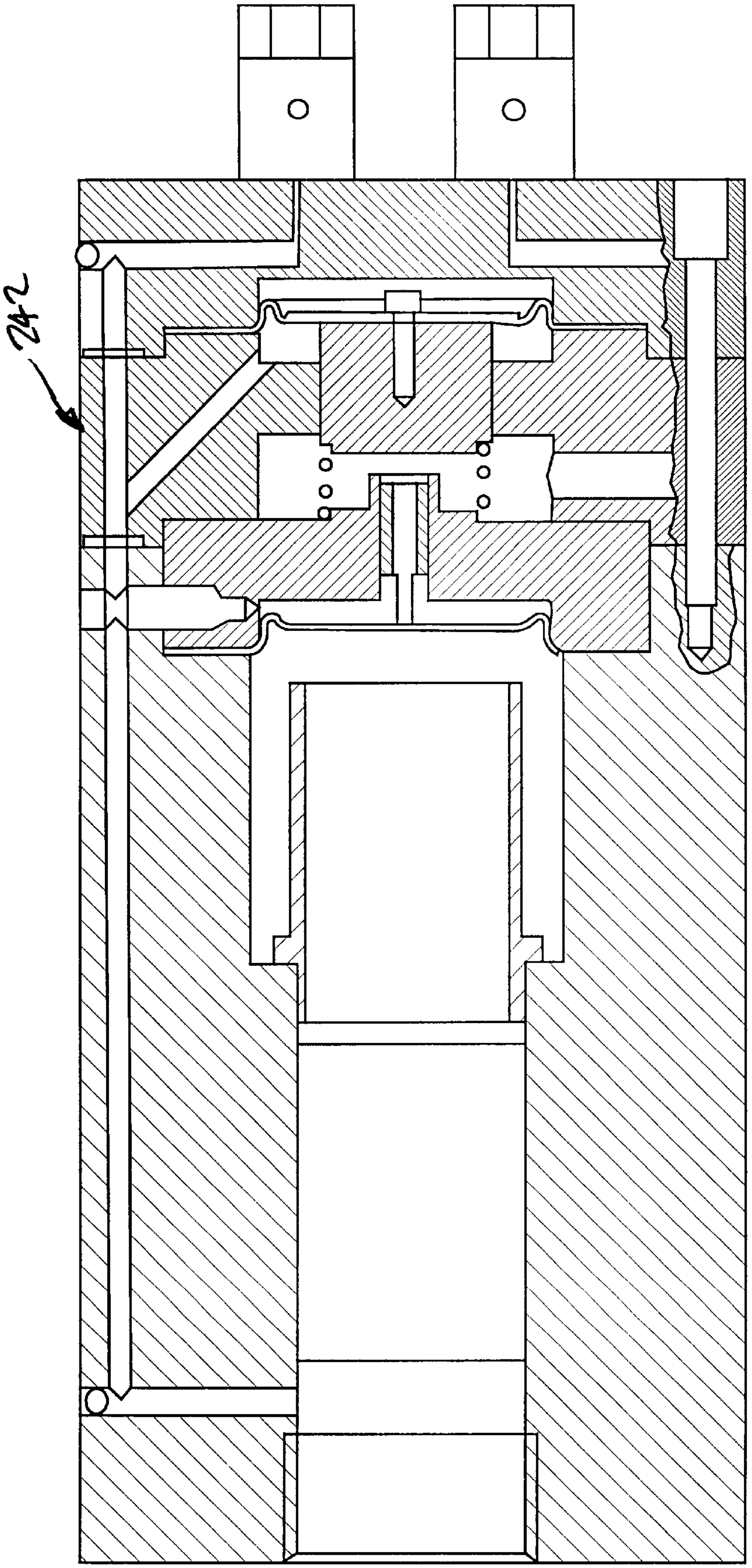

As illustrated in FIGS. 23 through 24, the exemplary pressure regulator assembly 242 is a dome load proportional control pressure relief valve, preferably providing for an adjustment range of approximately 1 to approximately 10 PSIG for the pressure tank 236 discussed above. Upon startup of the external counterpulsation apparatus 201, the pressure regulator valve dome is vented to atmosphere. Once the compressor comes on and begins to pressurize the pressure tank, the control valve portion of the pressure regulator is still wide open to the exhaust port, providing for minimum tank pressure built-up. The minimum tank pressure is supplied through a flow control orifice to the servo chamber and to the dome load solenoid. With no dome pressure, the servo chamber vent valve is open and exhaust the servo chamber pressure to local ambient pressure. The dome dump solenoid (normally open to local ambient) is powered "on", thus sealing the dome. The dome load solenoid is powered "on", and the dome pressure slowly increases, causing the dome diaphragm to move down, thus closing the servo vent valve. Servo chamber pressure now quickly increases, moving the servo diaphragm down and closing off the control valve. Pressure tank pressure now begins to increase.

At the desired pressure tank pressure, the power to the dome load solenoid is turned "off". The control valve now attempts to maintain the preset desired tank pressure. If the tank pressure increases, the dome diaphragm moves up, allowing the servo chamber vent valve to open. This reduces the servo pressure, allowing the control valve to open, thus reducing the increased tank pressure to the desired set point. The control servo chamber pressure will maintain the control valve at the opening extent that is necessary to maintain the desired preset, preselected tank pressure, thus allowing the compressor flow to exhaust into the muffled exhaust system. When the rotary solenoid inflation/deflation valves open, a sudden drop in tank pressure occurs. This sudden drop is sensed by the dome diaphragm which instantly moves down closing the servo vent valve. Immediately, the servo chamber pressure builds, causing the control valve to close so that the compressor can make up for the sudden tank pressure drop below the desired preset level. If operation of the subsequent inflatable cuff devices causes a drop in the tank pressure, the control valve stays closed so that the tank pressure can recover to the desired preset pressure level in the shortest possible time. When the inflatable cuff devices 208, 210 and 212 are exhausted, the tank pressure recovers quickly due to the fact that the compressor is constantly providing pressurized gas into the tank. When the desired tank pressure set point is reached, the dome diaphragm, sensing the increased tank pressure, moves up, thus opening the servo chamber vent valve and reducing the servo chamber pressure to a value that holds the control valve open at a position that maintains the tank pressure at the desired preset level and exhausts the compressor flow into the muffler and exhaust system.

Preferably the dome control solenoids operate at 24 volt DC 0.6 watts each. The orifice is preferably 0.031 inch in diameter, and the load and bleed solenoids are two-way two position solenoids, with the vent solenoid preferably being a three-way two position solenoid. The load dome is a two-way normally closed solenoid, using 24 volt DC to increase dome pressure. The bleed dome is a two-way normally closed solenoid, using 24 volt DC to decrease dome pressure. The dome vent port is open to dome pressure when the power is off, with power to the solenoid closing the vent port and allowing the dome pressure to increase. A power failure causes the vent port to open and vents the dome pressure, which correspondingly vents the tank pressure.

Figure 26:
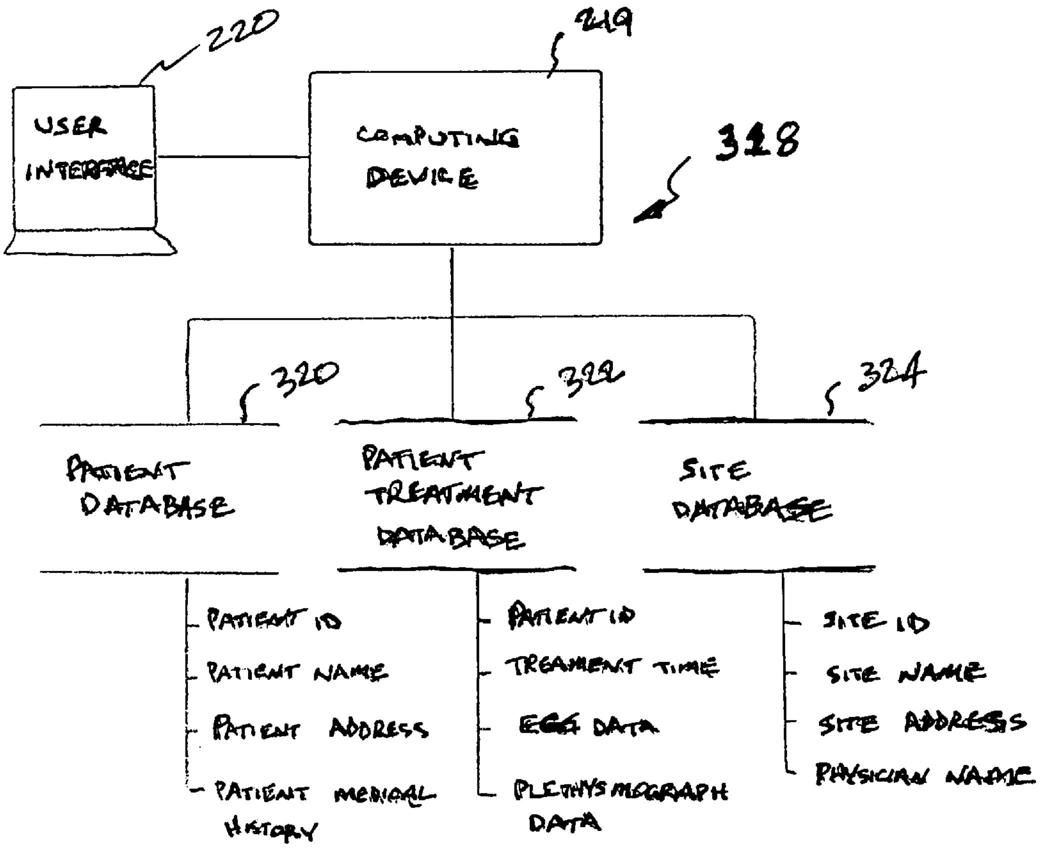
FIG. 26 is a block diagram depicting one enhanced computer system for monitoring and recording the treatment of a patient using an external counterpulsation device in accordance with the present invention.

FIG. 26 depicts an enhanced computer system 318 for monitoring and recording the treatment of a patient who is receiving treatment from the external counterpulsation device of the present invention. As previously described, the computing system 318 is used to control the operations of the external counterpulsation device. In accordance with another aspect of the present invention, the enhanced computer system 219 is further operable to monitor and record information associated with the treatment of the patient.

More specifically, the enhanced computer system 318 includes a patient database 320 for storing demographic information for one or more patients; a patient treatment database 324 for storing treatment information for one or more patients; a site database 324 for storing information regarding the site of the patient treatment; and a computing device 219. For illustration purposes, a preferred embodiment of the computing device 219 is a personal computer (PC) having an associated touch screen monitor and keyboard 220. In this case, the data structures are defined in a storage device associated with the personal computer (e.g., an internal hard drive).

FIGS. 27 through 30 illustrate some exemplary control screens that help to better understand the functionality of the enhanced computer system 320. As shown in FIG. 27, a main menu screen 326 allows the operator to select from one of four options: (a) patient information, (b) site information, (c) ECP Treatment, or (d) system diagnostics. The patient information and site information options allow the operator to enter patient information and clinical site information, respectively, into the system. The ECP treatment option allows the operator to monitor and control the treatment of a patient; whereas the system diagnostic option allows the operator to simulate treatment of a patient for purposes of training the operator and/or testing the equipment of the external counterpulsation device.

Figure 28:
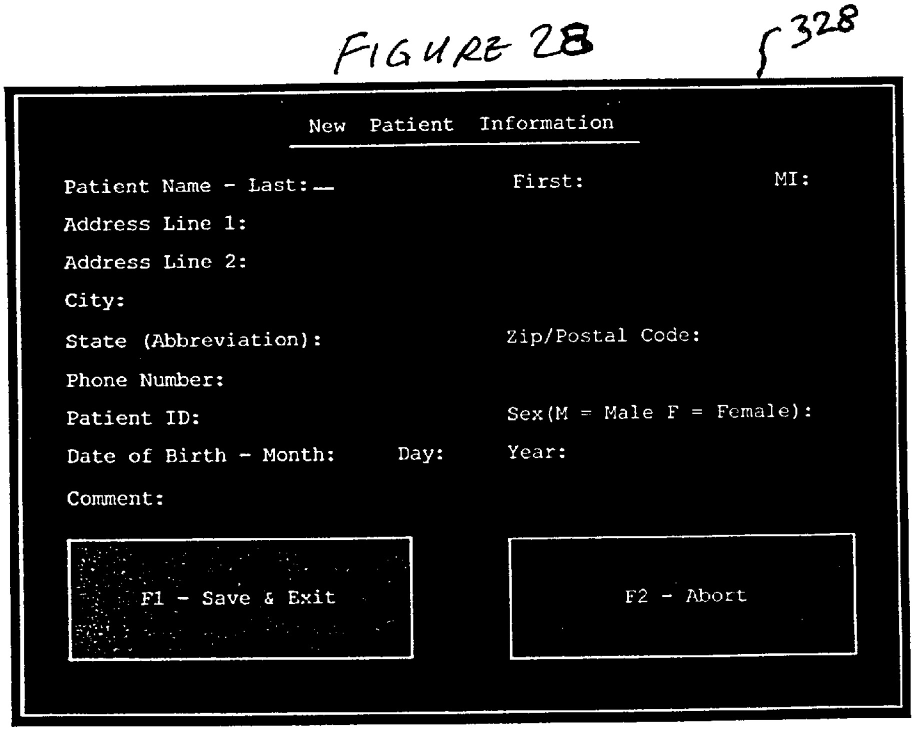
FIG. 28 illustrates an exemplary patient information screen for the enhanced computer system of the present invention.

Referring to FIG. 28, the patient information screen 328 permits the operator to input and/or edit demographic information for one or more patients. The patient demographic information may include (but is not limited to) the patient's name, address, phone number, sex, date of birth and other comments relating to the medical treatment of the patient (e.g., medication, disease history, etc.). Once this information is entered for a new patient, it may be stored into the patient data structure 320. Each new patient may also be assigned a randomly generated patient identification number that is stored in the patient data structure 320.

Figure 29:
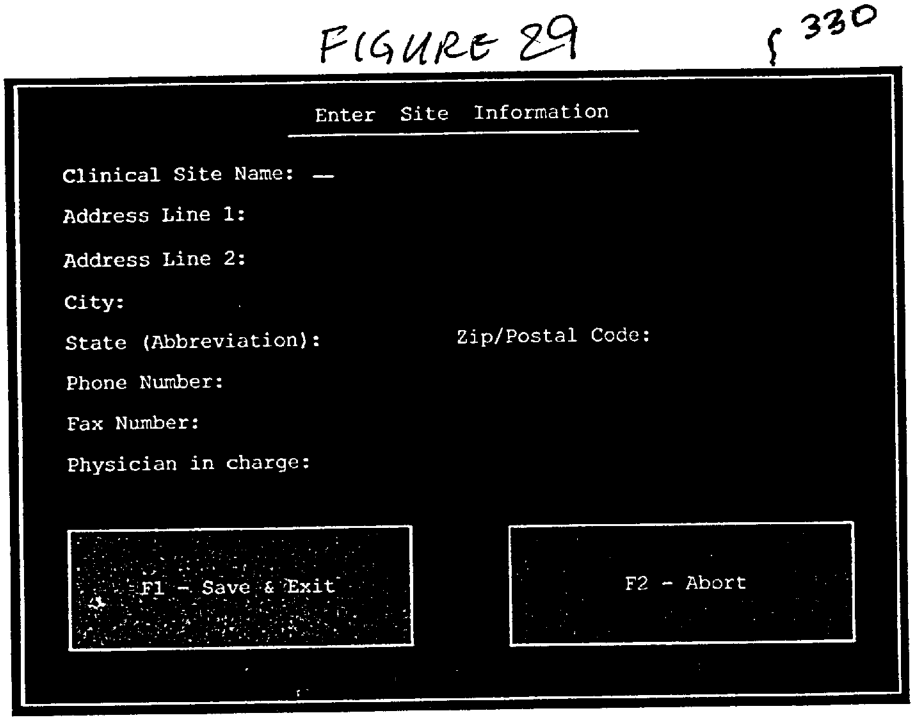
FIG. 29 illustrates an exemplary site information screen for the enhanced computer system of the present invention.

Similarly, the site information screen 330 permits the operator to input and/or edit information relating to the clinical site as shown in FIG. 29. The site information may include (but is not limited to) the clinical site's name, address, phone number, facsimile number, and the name of the physician associated with the clinical site. The site information is stored in the site information data structure 324.

FIG. 30 illustrates the primary treatment control screen 332 for monitoring and controlling the patient's treatment as provided by the external counterpulsation device of the present invention. At least some portion of the patient's demographic information 334 may be displayed in the upper left hand corner of the user interface. Along the top of the user interface are three operational buttons. A start button 336 allows the operator to start treatment to the patient. A standby button 338 allows the operator to pause or stop the treatment to the patient. It is envisioned that a pause in the treatment will allow the operator to connect ECG electrodes to the patient, set-up the inflation/deflation cycle, modify the inflation/deflation cycle or make other minor adjustments to the treatment process. An exit button 340 allows the operator to exit from the treatment mode.

Of particular importance, patient treatment information is prominently displayed in the center of the user interface. The upper waveform 342 is an electrocardiogram (ECG) signal taken from the patient. As will be apparent to one skilled in the art, the R wave portion of the ECG signal is typically used to monitor the cardiac cycle of the patient. The lower waveform 344 is a pressure signal indicative of the blood pressure of the patient. The pressure signal is also used to monitor the cardiac cycle of the patient as well as to monitor the counterpulsation waves being applied to the patient by the external counterpulsation device. In a preferred embodiment, the pressure signal is further defined as a plethysmograph waveform signal as received from a finger plethysmograph probe. Two amplitude adjustment switches 346 and 348 are positioned just to the right of each of these waveforms which allow the operator to adjust the resolution at which the signals are viewed.

A timing signal 350 is simultaneously displayed between the upper and lower waveforms. The timing signal 350 indicates when the inflation/deflation cycle is being applied to the patient by the external counterpulsation system. More specifically, the timing signal includes a timing bar for each inflation/deflation cycle, where the leading edge of the timing bar corresponds to the initiation of inflation and the trailing edge of the timing bar corresponds to the initiation of deflation.

As is well known, the safety and effectiveness of the external counterpulsation therapy depends on the precise timing of the inflation/deflation cycle in relation to the cardiac cycle of the patient. For instance, an arterial wall with significant calcium deposits (hardened artery) will transmit the external pressure pulse up the aorta faster than an elastic vasculature. Therefore, the inflation valves should be opened later for a calcified artery than for a normally elastic artery. Since it is difficult to measure the elasticity of the arterial wall, the operator may have to manually adjust the proper timing of the inflation valves by imposing the requirement that the arrival of the external pulse at the root of the aorta be after the closure of the aortic valves. The enhanced display of the three patient treatment signal enables the operator to more accurately adjust the timing of the inflation valves. This is one exemplary way in which the enhanced computer system of the present invention improves the patient treatment provided by the external counterpulsation device.

To further improve the monitoring of the timing of the inflation/deflation cycle in relation to the cardiac cycle of the patient, timing markers 352 may be superimposed over the ECG signal. The timing markers 352 appear for each interval of an QRS wave on the ECG signal. The markers represent time intervals in the QRS wave, for example, at 5 ms intervals, to facilitate accurate and precise calibration of inflation and deflation in relation to the QRS wave. As will be apparent to one skilled in the art, the amplitude of the signals are adequately sized so that the markers may not be misinterpreted as noise associated with the ECG signal. The timing markers switch 354 allows the operator to turn on/off the display of the timing markers on the screen.

The treatment control screen 332 also provides the switches for adjusting the timing of the inflation/deflation cycle. An inflation adjustment switch 356 allows the operator to adjust the setting of the time for the start of the sequential cuff inflation as it is measured relative to the R peak of the ECG signal. Each press of the left arrow causes the inflation to occur some predefined time increment earlier (e.g., 10 ms); whereas the right arrow causes the inflation to occur some predefined time increment later. The current setting of the inflation start time is displayed on the middle window of the switch 356. Likewise, a deflation adjustment switch 358 allows the operator to adjust the setting of the time for the start of deflation as it is measured relative to the R peak of the ECG signal.

In addition, the treatment time for the patient is monitored and controlled by two additional interfaces. A treatment setting switch 360 allows the operator to set the time for the patient treatment. Again, each press of the left arrow causes an increase in the treatment time by some predefined time increment (e.g., 1 minute) and each press of the down arrow decreases the treatment time by the same predefined time increment. The current setting of the treatment time is displayed on the middle window of the switch 254. An elapsed treatment time display 362 shows the elapsed time of the current treatment session.

Other patient treatment information may also be displayed and/or adjusted through the use of the treatment control screen 332. For instance, a heart rate display 364 may show the heart rate of the patient and a diastolic/systolic ratio display 368 may show the peak ratio and the area ratio of the plethysmograph signal. Additionally, a pressure adjustment switch 370 may be provided to allow the operator to adjust the inflation pressure of the compressed air. It is envisioned that other patient treatment information may be displayed and/or adjusted through various user interfaces as provided on the treatment control screen 332.

As described above, the enhanced computer system 318 is operable to receive and store various information relating to the treatment of patients using an external counterpulsation device. For instance, a patient record may be created for each patient prior to that patient receiving any treatment. The patient information may then be used to update an international registry (e.g., IEPR). As is well known, the registry helps to determine patterns of use, safety and efficacy of external counterpulsation therapy. It is envisioned that the enhanced computer system 200 may be adapted to transmit patient information over a network channel to a registry application residing on another computer system.

At each treatment session, a patient's record can be recalled and displayed on the treatment control screen 326. During treatment, the patient's treatment information may be captured and stored in the patient treatment database 322. In a preferred embodiment, elapsed treatment time is recorded for the current treatment session. This elapsed treatment time may then be used to update an accumulated treatment time that is stored for each patient. A more detailed treatment history may also be captured for each patient. For instance, data representative of the ECG signal and/or the plethysmograph signal may be stored in the patient treatment database. In addition, data indicative of the inflation/deflation cycle may be captured and stored in the patient treatment database 322. It is envisioned that other types of treatment information (e.g., inflation pressure, patient heart rate, etc.) may also be captured and stored in the patient treatment database 322.

Again, the enhanced computer system 218 may be adapted to communicate the patient treatment information over a some type of communication link (e.g., satellite link, Internet, etc.) to another computer system. In this way, the patient treatment data from various clinical sites may be accumulated for subsequent statistical analysis which is intended to improve the external counterpulsation treatment process. For example, the accumulated treatment data may be used to determine what patient characteristics predict a successful response to external counterpulsation therapy. It is also envisioned that a patient's treatment information may be transmitted in real-time to another clinical site. In this case, the patient treatment information may be view by a more experienced technician or physician who could remotely assist in the treatment process. Alternatively, the patient treatment information may be used for remote training purposes, and such communication with another computer system can be used to transfer updated software, service and maintenance related information, or operator assistance or training information, for example.

Figure 31:
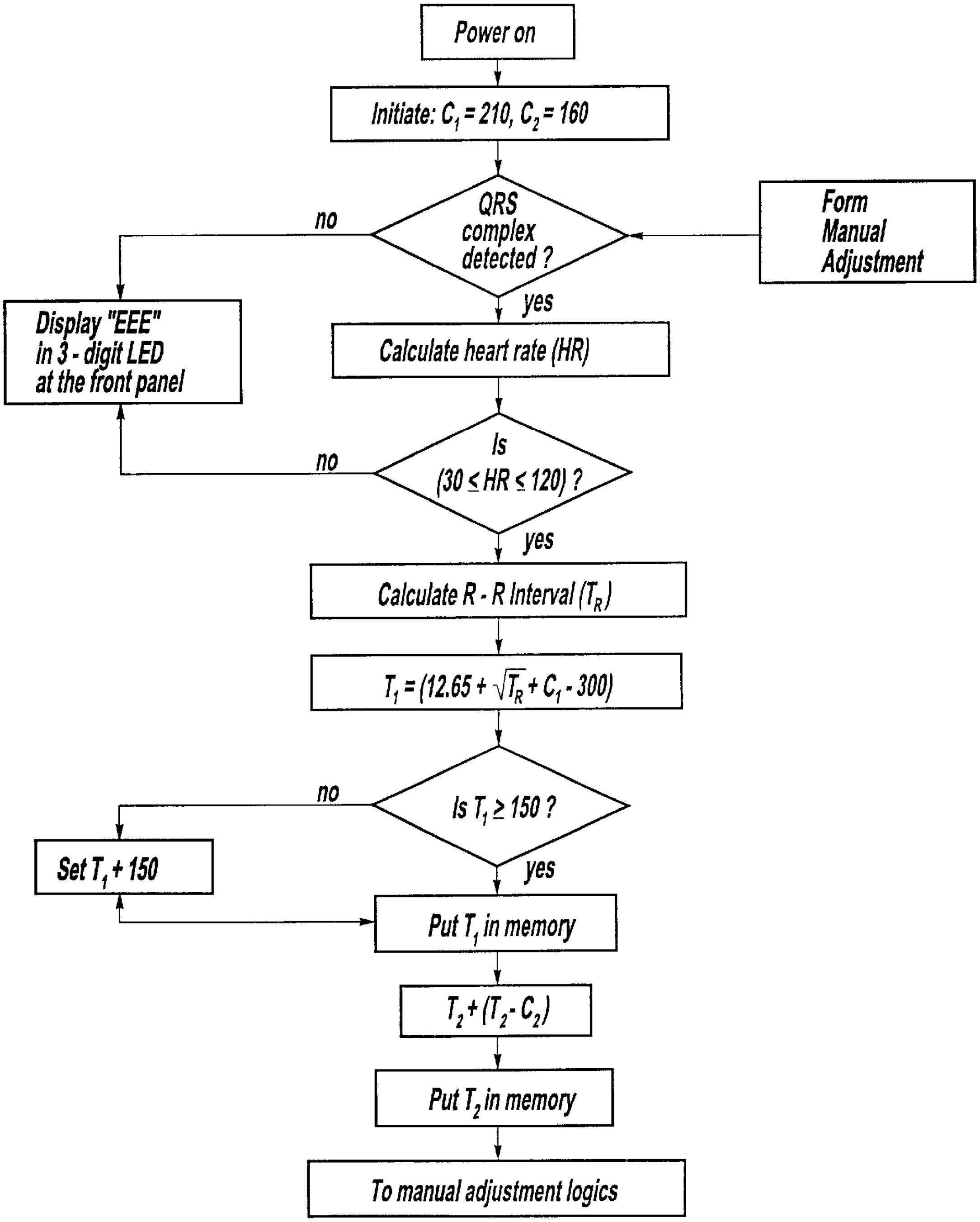
FIG. 31 diagrammatically illustrates initiation timing logics for the inflation/deflation valves of the external counterpulsation apparatus of FIGS. 1 through 30.

FIG. 31 is a block diagram or flow chart summarizing the procedures of the initiation operation and the automatic set up of the inflation/deflation logic for the external counterpulsation apparatus 201. It important to note that the actual opening of the inflation/deflation valves are performed by a power switch circuit which reads the values of $T_1$ and $T_2$ from memory. It should also be noted that even though the inflation time $T_1$ appears to be relatively short, i.e. less than one-half of the R-R interval, it represents the time at which the inflation signal is being sent to the power switching circuit to initiate opening of the inflation valves. It takes approximately 20 msec for the valves to fully open, another thirty msec for the air pressure to arrive at the inflatable cuff devices, and an additional two hundred to three hundred msec for the applied pressure to transmit through the vasculature from the legs and thighs to the root of the aorta. By that time, the systolic period would have already passed. In addition, it can be shown that the deflation time always happens one hundred sixty msec before the next R wave. Deflation valves for the lower leg and thigh cuffs open to the atmosphere for a duration of one hundred twenty msec. Since the decay time $T_4$ is 80 msec at the most for the inflation cuff device pressure to drop to zero, there is no residual pressure existing in the cuffs at the beginning of the next systolic phase, giving the peripheral vascular bed ample time to refill during cardiac systole.

During the operation stage following the initiation stage, the values of $_{T1}$. and $T_2$ will be stored in memory and used to control the inflation/deflation timing. However, the memory will be updated with every new heartbeat using the updated $T_R$ to calculate the new $T_1$ and $T_2$ and stored in memory replacing the old $T_1$ and $T_2$. In addition, the CPU will interrogate every 10 ms a flag in one of the registers to determine if any of the manual adjustment buttons have been pushed. The four inflation/deflation adjustment buttons are located on the front panel (screen) for advancing or retarding the inflation or deflation times.

Each depression of the inflation advance button will trigger the CPU to compare the vale $(T_R-T_1)$ to 200 ms. If $(T_R-T_1)$ is larger than 200 ms, then $T_1$ will be lengthened by 10 ms. This is done by adding 10 ms to $C_1$ which has been initially set at 210 ms as used in $T_1=(12.65*T_R+C.-300)$ ms. The same logical procedure is done to limit the ability of advancing $T_1$ to 200 ms or less before the next R wave, in order to prevent the inflation valve of the lower leg cuffs from opening so late that not enough time remains for the deflation valves to open before the next R wave; keeping in mind the facts that the inflation valve for the thigh cuffs opens 50 ms after $T_1$ and remains open for another 100 ms, leaving only 50 ms for the pair of deflation valves to open before the next R wave. Since the logic used in controlling the manual adjustment of the deflation valves sets a limit for the deflation to open no later than 30 ms before the next R wave, it is clear that the deflation valves will have to open to the atmosphere within 30 ms after the inflation valve of the thigh cuffs is closed.

The other three manual inflation/deflation adjustment buttons work on the same principle; that is, with each depression of one of the buttons, the CPU will check the conditions limiting the timing of the valves, and if the limits are not reached, then the timing for the inflation/deflation valves can be advanced or retreated by subtracting or adding 10 ms to $C_1$ or $C_2$ of the above equation and the equation $T_2=(T_R-C_2)$ ms.

The formula used in calculating $T_1$ is given by:

$$T_1=(12.65*T_R+C_1-300)\text{ms}$$

where the constant 12.65 is used instead of 0.4 when converting the unit of $T_R$ from s to ms, and $C_1$ is a constant that is initially assigned with a value equal to 210 ms. However, this value can be changed later by manual adjustment. The factor 300 ms has been experimentally determined to be equal to the average time it takes for the applied external pressure wave to travel from the lower leg to the aortic valves.

After $T_1$ has been determined, it is comprised with a value of 150. If $T_1$ is less than 150 ms, it is then set to 150 ms. If Ti is larger than 150 ms, then the calculated value will be used. These procedures guarantee that the inflation valves will not open in less than 150 ms after the R wave.

Once the value of $T_1$ has finally been determined, it is used to calculate $T_2$ using the following formula:

$$T_2=(T_R-C_2)\text{ms}$$

where the constant $C_2$ is initially set at 160 ms and can be increased or decreased later by manual adjustment. From this equation, it is clear that the deflation valves open 160 ms before the next R wave.

In conclusion, the logic used in the timing of the inflation/deflation valves have fulfill two basic criteria: the inflation valves must not be opened during the cardiac systolic period so that there is no systolic loading; the deflation valves must be opened to the atmosphere before the next R wave to allow enough time for the air pressure in the cuffs to decay to zero so that there is no residual pressure causing a tourniquet effect. Finally, it is important to note that the inflation/deflation valves will not be operational when the heart rate is higher than 120 beat/min or than 30 beat/min.

Figure 32:
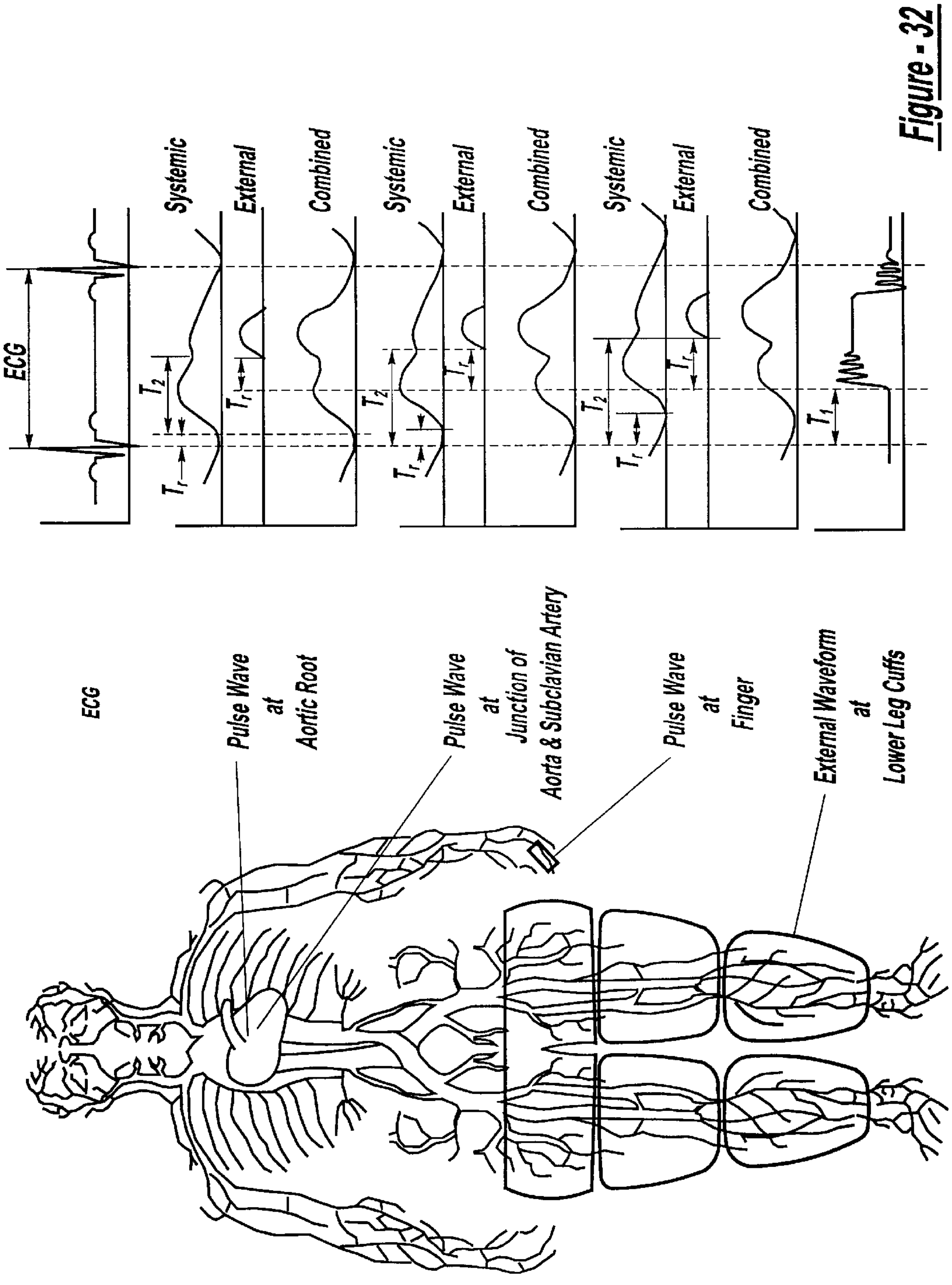
FIG. 32 is a diagrammatic representation of the timing relationships between aortic root pressure and finger plethysmography waveforms.

Optimal timing for maximum diastolic augmentation is to apply the external pressure such that the applied wave-front arrives at the root of the aorta just after the closure of the aortic valves. Since the effect of diastolic augmentation is monitored at the fingertip with a photoelectric plethysmorpragh, it is important to understand the timing relationship of the applied pressure waveform detected by the finger plethysmorgraphy and that at the aortic root. FIG. 32 shows the pressure waves at different location relative to the QRS complex.

The periods are defined as:

$T_{RR}$: R-R interval, the time for one complete heart beat;

$T_{A1}$: from QRS complex to the rise of systemic pressure in the aortic root; this usually represents the time for isometric contraction of the left ventricle;

$T_{A2}$: from QRS complex to the closure of the aortic valves (end systole) at the roof of the aorta;

$T_{A3}$: from the time the lower leg inflation valve opens to the time when the external waveform first appears at the root;

$T_{J1}$: from QRS complex to the rise of systemic pressure at the junction of the aorta and the subclavian artery;

$T_{J2}$: from QRS complex to end systole at the junction of aorta and subclavian artery;

$T_{J3}$: from the opening of the lower leg inflation valve to the arrival of the external pulse at the aortic-subclavian junction;

$T_{F1}$: from QRS complex to the rise of the systemic pressure at the finger tip detected by photoelectric plethysmography;

$T_{F2}$: from QRS complex to end systole detected at finger;

$T_{F3}$: from the lower leg inflation valve opening to the arrival of external pressure waveform at finger;

$T_1$: from QRS complex to the lower leg inflation valve opening.

As shown in FIG. 32, the external pressure is applied at time $T_1$ after the QRS complex. This pulse will travel up the aorta towards the heart. By the time it reaches the junction of the aorta and the subclavian artery $T_{J3}$ later, part of the pulse will combined with the systemic blood pressure wave and travel down the subclavian artery to the finger tip, arrived at a time $T_{F3}$ later. Since the systemic pressure and the applied pulse are traveling at the same velocity, the phase relationship of the combined wave will remain the same as that at the junction when it reaches the finger. Conversely, if diastolic augmentation is timed by observing the combined wave at the finger such that $T_{F3}$ coincides with $T_{F2}$. In other word, if the external pressure waveform arrives at the fingertip just after end systole, then the same phase relation will hold at the aorta-subclavian junction.

Meanwhile, when the external pulse is traveling down the subclavian artery, another part of it will travel down the ascending aorta to the root, and arrive at a time $T_{A3}$ after the opening of the inflation valve. Since the external pulse reaches the aorta-subclavian junction before it reaches the aortic root, $T_{A3}$ is longer than $T_{J3}$. Therefore if the external waveform is timed to arrive at the finger plethysmography direct after end systole, then it will arrive at the aortic root just a short time later, a delay equals to the time it takes for the systolic wave to travel the short distance of the ascending aorta from the root to the aortic-subclavian junction plus the time for the external pulse to travel from the junction to the root. This delay is usually a few milliseconds and can be considered negligible.

In summary, by considering the transmission of the pressure wave in the vasculature, it can be shown that if the applied external pressure waveform arrives at the finger after end systole, the same phase relationship between the systolic pressure and the external waveform will hold true at the root of the aorta.

The inflation/deflation valve timing logic controls the timing of external pressure applied to the lower legs and thighs of the patient. A diagram of how the inflation/deflation valves are connected to the compressor and air tank is shown in FIG. 9.

The inflation/deflation timing logic is divided into two main parts; the initiation stage upon power up during which the inflation/deflation times are set up automatically, and the operation stage during which the inflation and deflation time can be adjusted manually. The operations of these timing logic systems are controlled by a microprocessor (Z-80), and no signal will be sent out to the inflation/deflation valve power supply when the heart rate is higher than 120 beat/min or lower than 30 beats/min.

There are three inflation valves and three deflation valves. One pair of inflation/deflation valves are for the calves, one pair for the lower thighs and one pair for the upper thighs. The valves are normally closed, and open when energized. Upon receipt of a signal from the inflation/deflation timing control, electrical power to the inflation valves will be switched on for a period of 100 ms and will open them to the air tank. Similarly, upon receipt of the deflation valve signal, power to the deflation valves will be switched on for a period of 120 ms and will open the lower leg and thigh cuffs to the atmosphere. In addition, two safety valves can be provided, each of them located between the inflation valve and the cuffs. The safety valves are normally open to air. These two optional valves (not shown) are independent of the logic controlling the inflation/deflation valves. They are installed in case of power failure so that pressure remaining in the leg and thigh cuffs can be vented to the atmosphere automatically.

During initiation stage when power is turned on, the central process unit (CPU), a microprocessor Z-80, at the control console will start a series of initiation procedures. The first step is to open the deflation valves to air. Each opening of the deflation valve will last for 120 ms and has been experimentally determined to be long enough to relieve all the air pressure from the leg and thigh cuffs. Then the CPU will look for the input of the electrocardiogram (ECG) and determine the presence of the QRS complex. If no QRS complex has been detected, the inflation/deflation valves will not be activated and the external counterpulsation will not start. The inflation valves will remain closed; no air will enter the cuffs from the reservoir.

After the detection of four complete R-R intervals, the CPU will determine their average ($T_R$), and will update $T_R$ by taking the mean of the last $T_R$ and the new R-R interval. Meanwhile, the two constants used for the calculation of inflation time $T_1$ and deflation time $T_2$ will be initiated with the values $C_1$=210 ms and $C_2$=160 ms. Definitions of $T_1$ and $T_2$ and other variables are shown diagrammatically in FIG. 33. They are:

$T_R$(R-R interval): average R-R interval in ms.

$T_1$ (inflation time): interval from R wave to the opening of lower leg inflation valve in ms. Note that the inflation valve for the thigh cuffs open 50 ms after $T_1$. In addition, inflation valves are normally closed. However, they will be opened for a duration of 100 ms when energized.

$T_D$(duration time): interval between the opening of the lower leg inflation valve and the opening of the deflation valves for both the lower legs and thighs in ms.

$T_2$(deflation time): interval from R wave to the opening of the deflation valves in ms. Note that the deflation valves for both lower leg and thigh cuffs are normally closed. They will be opened to the atmosphere for 120 ms when energized. This opening time has been experimentally determined to be at least 40 ms longer than the pressure decay time $T_4$.

$T_3$(pressure rise time): interval between the time when the air pressure in the lower leg or thigh cuffs is zero and the time when it reaches equilibrium with the pressure in the reservoir. This value has been measured experimentally under many different situations with various cuff sizes and is equal to 50 ms.

$T_4$(pressure decay time): interval for the air pressure in the cuffs to drop to zero when the deflation valves are opened to the atmosphere. The value of $T_4$ has been determined in a variety of situations with various cuff sizes and has an average value of 80 ms.

Figure 33:
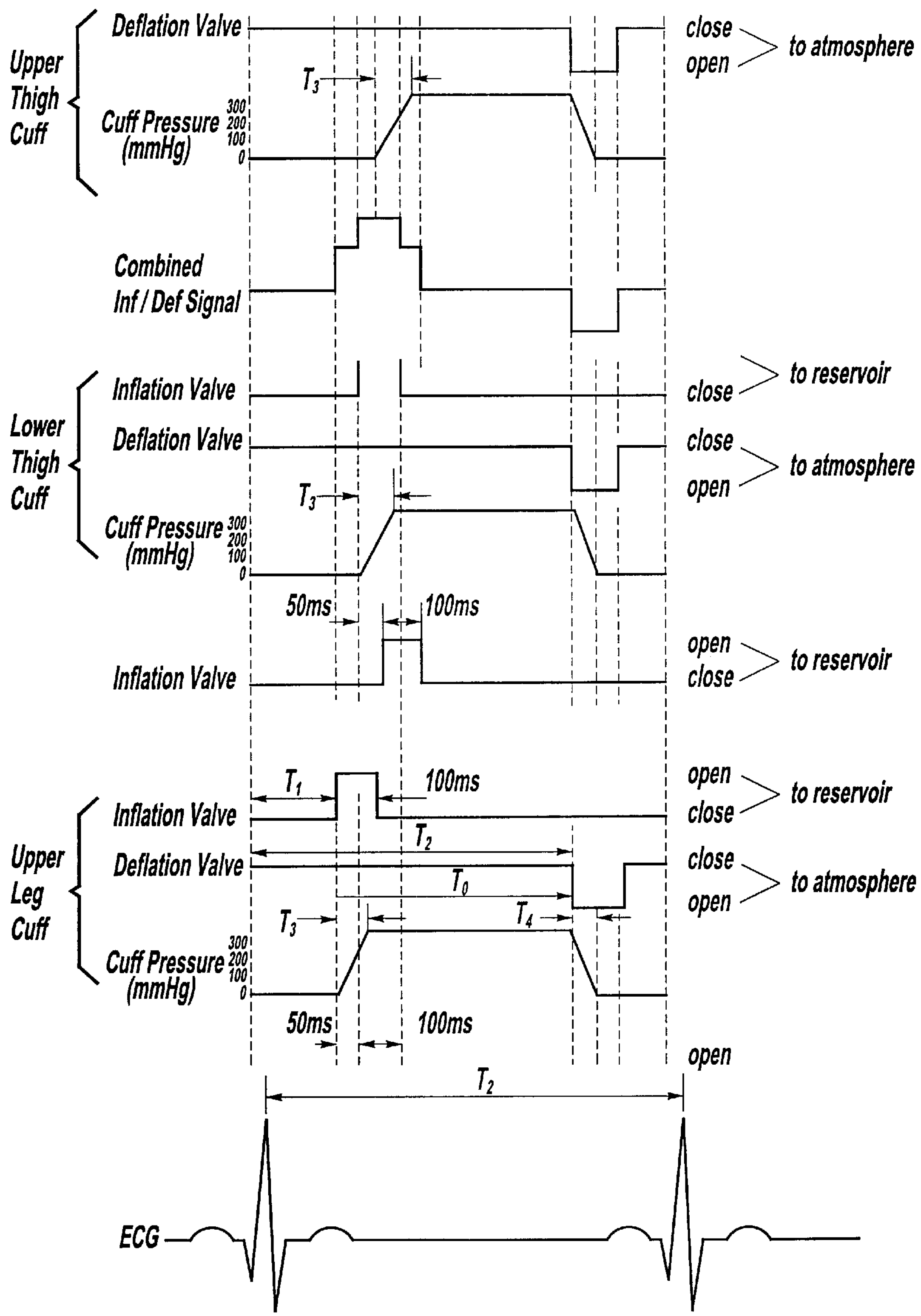
FIG. 33 is a diagrammatic representation of the timing for the inflation/deflation valves and the air pressure waveforms in the inflatable cuff devices of the counterpulsation apparatus of FIGS. 1 through 32.

A diagrammatic representation of the time for inflation/deflation valves and air pressure waveforms for the three pair of cuffs shown in FIG. 33. The patient electrocardiogram (ECG) using a 3-lead system is digitized and the R-R interval $T_R$ determined. The R-wave is then used as a triggering signal. The inflation time $T_1$ for the lower leg cuffs is calculated according to the square root formula of Bazett (see FDA 510(K) submission K882401):

$$T_1=(12.65*T_R+C_1-300)\text{ms}$$

where $C_1$ is a constant with an initial value of 210 ms. The inflation time can be adjusted manually, and the adjustment changes the $C_1$ value. Therefore application of external pressure to the body begins with the lower leg $T_1$ ms after the QRS complex. Inflations of the lower thigh cuffs begin 50 ms after the inflation of the lower leg cuffs, and the upper thigh cuffs will be inflated 50 ms after the lower thigh cuffs.

The initial value assigned to $T_1$ (as discussed above) is based on the square root formula of Bazett (Heart 7:353, 1920) which approximates the normal Q-T interval of the ECG as the product of a constant (0.4) times the square root of the R-R interval measured in seconds. The Q-T interval is measured from the beginning of the QRS complex to the end of the T wave. It represents the duration of ventricular electrical systole and varies with the heart rate; it can be used to approximate the hemodynamic systolic interval.

The operation of the improved external counterpulsation apparatus 201 of FIGS. 8 through 33 is explained further in the attached APPENDIX—EECP® THERAPY SYSTEM MODEL T53, OPERATION MANUAL, which is incorporated herein as part of this specification.

The foregoing discussion discloses and describes merely exemplary embodiments of the present invention for purposes of illustration. One skilled in the art will readily recognize from such discussion, and from the accompanying drawings and claims, that various changes, modifications, and variations can be made therein without departing from the principles, spirit or scope of the invention as defined in the following claims.

What is claimed is:

1. An external counterpulsation apparatus for treating a patient, comprising:

a balloon assembly adapted to be received about the lower extremities of the patient, said balloon assembly including a plurality of inflatable devices;

a source of compressed fluid;

a fluid reservoir interconnected with said source of compressed fluid for inflating said inflatable devices; and a fluid distribution assembly interconnected with said fluid reservoir for distributing compressed fluid from said source of compressed fluid to said inflatable devices;

said fluid distribution assembly including a selectively operable inflation/deflation valve interconnected between each of said inflatable devices and said fluid reservoir, each of said inflation/deflation valves having a pneumatically actuable power operator thereon and being interconnected with said balloon assembly and separately operable such that each of said inflatable devices is separately sequentially inflatable and deflatable, each of said inflation/deflation valves having an input interconnected with said fluid reservoir, an inflation/deflation port interconnected with one of said inflatable devices, and a deflation exhaust port in fluid communication with the atmosphere, said deflation exhaust port being normally open so as to default to said normally open condition upon loss of power to said power operator.

2. An apparatus according to claim 1, further including a movable table upon which the patient is situated during treatment, said inflation/deflation valves being attached to said movable table for movement therewith.

3. An apparatus according to claim 2, wherein said movable table is movable upon a plurality of wheels attached thereto.

4. An apparatus according to claim 2, wherein said inflation/deflation valves are mounted on an underside of said table, and the patient being situatable upon an upper side of said table.

5. An apparatus according to claim 2, wherein said table further includes an articulatable portion thereof and a main portion thereof allowing selective angulation of said articulatable portion with respect to said main portion.

6. An apparatus according to claim 5, wherein said table includes a power-operable elevation assembly selectively operable to adjust the height thereof.

7. An apparatus according to claim 1, further including a computer-implemented system for recording patient information for the patient receiving the treatment, said computer-implemented system including:

a patient data structure for storing demographic information for one or more patients receiving treatment;

a patient treatment data structure for storing treatment information for one or more patients receiving treatment; and a computing device connected to the apparatus for controlling operation of the apparatus, said computing device further operative to receive at least one of demographic information and treatment information and to store the information in the corresponding patient data structure or patient treatment data structure.

8. An apparatus according to claim 7, wherein said computing device is receptive of patient demographic information and operable to store the patient demographic information into the patient data structure.

9. An apparatus according to claim 8, wherein the patient demographic information includes a patient identifier, a patient name, and at least some patient medical data.

10. An apparatus according to claim 7, wherein the computing device is receptive of patient treatment information and operable to store the patient treatment information into the patient treatment data structure.

11. An apparatus according to claim 10, wherein the patient treatment information includes at least one of ECG data from the patient, blood pressure data from the patient, heart rate data from the patient and inflation/deflation cycle data associated with the external counterpulsation device.

12. An apparatus according to claim 7, wherein the computing device is adapted to communicate at least one of the patient demographic information and the patient treatment information over a communication link to a second computing device.

13. An apparatus according to claim 7, wherein said computing device controls the distribution of the compressed fluid to the balloon assembly, thereby inflating and deflating the inflatable devices.

14. An external counterpulsation apparatus for treating a patient, comprising:

a balloon assembly adapted to be received about the lower extremities of the patient, said balloon assembly including a plurality of inflatable devices;

a source of compressed fluid;

a fluid reservoir interconnected with said source of compressed fluid for inflating said inflatable devices; and a fluid distribution assembly interconnected with said fluid reservoir for distributing compressed fluid from said source of compressed fluid to said inflatable devices;

said fluid distribution assembly including a selectively operable inflation/deflation valve interconnected between each of said inflatable devices and said fluid reservoir, each of said inflation/deflation valves having a power operator thereon and being interconnected with said balloon assembly and separately operable such that each of said inflatable devices is separately sequentially inflatable and deflatable, each of said inflation/deflation valves having an input interconnected with said fluid reservoir, an inflation/deflation port interconnected with one of said inflatable devices, and a deflation exhaust port in fluid communication with the atmosphere, said deflation exhaust port being normally open so as to default to said normally open condition upon loss of power to said power operator, wherein each of said inflation/deflation valves is a rotary actuable valve.

15. An external counterpulsation apparatus for treating a patient, comprising:

a balloon assembly adapted to be received about the lower extremities of the patient, said balloon assembly including a plurality of inflatable devices;

a source of compressed fluid;

a fluid reservoir interconnected with said source of compressed fluid for inflating said inflatable devices; and a fluid distribution assembly interconnected with said fluid reservoir for distributing compressed fluid from said source of compressed fluid to said inflatable devices;

said fluid distribution assembly including a selectively operable inflation/deflation valve interconnected between each of said inflatable devices and said fluid reservoir, each of said inflation/deflation valves having a power operator thereon and being interconnected with said balloon assembly and separately operable such that each of said inflatable devices is separately sequentially inflatable and deflatable, each of said inflation/deflation valves having an input interconnected with said fluid reservoir, an inflation/deflation port interconnected with one of said inflatable devices, and a deflation exhaust port in fluid communication with the atmosphere, said deflation exhaust port being normally open so as to default to said normally open condition upon loss of power to said power operator, wherein each of said inflation/deflation valves is a rotary actuable butterfly valve.

16. An apparatus according to claim 15, wherein each of said rotary actuable butterfly valves includes a rotatable rotor and a butterfly valve element rotatably attached to said rotor for rotation therewith, said rotor being rotatable through a maximum rotation angle of approximately 60 degrees between open and closed positions of said butterfly valve element.

17. An apparatus according to claim 16, wherein each of said rotary actuable butterfly valves includes a pair of said butterfly valve elements attached to said rotor for rotation therewith, a first of said butterfly valve elements being in fluid communication between said input and said inflation/deflation port and being normally closed, and a second of said butterfly valve elements being in fluid communication between said deflation exhaust port and said inflation/deflation port and being normally open.

18. An apparatus according to claim 17, wherein an inflation passageway through each of said butterfly valves between said input port and said inflation/deflation port is more restricted than a deflation passageway between said inflation/deflation port and said deflation exhaust port.

19. An external counterpulsation apparatus for treating a patient, comprising:

a balloon assembly adapted to be received about the lower extremities of the patient, said balloon assembly including a plurality of inflatable devices;

a source of compressed fluid;

a fluid reservoir interconnected with said source of compressed fluid for inflating said inflatable devices; and a fluid distribution assembly interconnected with said fluid reservoir for distributing compressed fluid from said source of compressed fluid to said inflatable devices;

said fluid distribution assembly including a selectively operable inflation/deflation valve interconnected between each of said inflatable devices and said fluid reservoir, each of said inflation/deflation valves having a power operator thereon and being interconnected with said balloon assembly and separately operable such that each of said inflatable devices is separately sequentially inflatable and deflatable, each of said inflation/deflation valves having an input interconnected with said fluid reservoir, an inflation/deflation port interconnected with one of said inflatable devices, and a deflation exhaust port in fluid communication with the atmosphere, said deflation exhaust power being normally open so as to default to said normally open condition upon loss of power to said power operator;

said source of compressed fluid including a compressor, said apparatus further including a power ramp-up device that upon startup of said apparatus converts electrical power to said compressor from 110/120 VAC 50/60 hz to three-phase 220 VAC at a variable frequency and increases the electrical power to a preselected full power level over a period of approximately three to approximately five seconds.

20. A method for monitoring the treatment of a patient who is receiving treatment from an external counterpulsation system, comprising the steps of:

displaying an electrocardiogram (ECG) signal taken from the patient;

displaying a plethysmograph waveform signal taken from the patient; and displaying a timing signal that is indicative of an inflation/deflation cycle of the external counterpulsation system.

21. A method for monitoring the treatment of a patient who is receiving treatment from an external counterpulsation system, comprising the steps of:

displaying an electrocardiogram (ECG) signal taken from the patient;

displaying a pressure signal indicative of the blood pressure of the patient; and displaying a timing signal that is indicative of an inflation/deflation cycle of the external counterpulsation system, said timing signal displaying a timing bar for each inflation/deflation cycle, wherein a leading edge of the timing bar corresponds to the initiation of inflation and a trailing edge of the timing bar corresponds to the initiation of deflation.

22. The method of claim 21, further comprising the step of adjusting the timing of the inflation/deflation cycle of the external counterpulsation system.

23. The method of claim 21, wherein the external counterpulsation device further comprises:

at least one adaptable balloon device adapted to be received about a lower extremity of the patient;

a fluid distribution device connected to the balloon device for distributing a compressed fluid thereto; and a computing device connected to the fluid distribution device for controlling the distribution of the compressed fluid to the balloon device, thereby inflating and deflating the balloon device.

* * * * *